US006804988B2

(12) United States Patent
McNamara et al.

(10) Patent No.: US 6,804,988 B2
(45) Date of Patent: *Oct. 19, 2004

(54) GOLF BALL COR TESTING MACHINE

(75) Inventors: Michael P. McNamara, Fairhaven, MA (US); Michael F. Vieira, Acushnet, MA (US); Laurent Bissonnette, Portsmouth, RI (US)

(73) Assignee: Acushnet Company, Fairhaven, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/428,750

(22) Filed: May 5, 2003

(65) Prior Publication Data

US 2003/0209053 A1 Nov. 13, 2003

Related U.S. Application Data

(63) Continuation-in-part of application No. 09/955,124, filed on Sep. 19, 2001, now Pat. No. 6,571,600.

(51) Int. Cl.$^7$ ................................................. G01N 3/30
(52) U.S. Cl. ...................................... 73/12.02; 73/65.3
(58) Field of Search ........................... 73/12.01, 12.02, 73/12.09, 12.1, 12.04, 12.07, 12.08, 78, 79, 82

(56) References Cited

U.S. PATENT DOCUMENTS

| | | | |
|---|---|---|---|
| 3,093,995 A | 6/1963 | Gordon ........................... 73/13 |
| 3,364,751 A | 1/1968 | Cornell et al. ................ 73/432 |
| 3,509,736 A | 5/1970 | Saari .............................. 73/13 |
| 3,677,546 A | 7/1972 | Oetiker .................... 273/102.2 |
| 3,814,438 A | 6/1974 | Baron et al. ................. 273/176 |
| 3,999,756 A | 12/1976 | Head ............................ 463/64 |
| 4,071,242 A | 1/1978 | Supran ......................... 273/61 |
| 4,289,023 A | 9/1981 | Rader ........................ 73/12.09 |
| 5,221,082 A | 6/1993 | Curshod ..................... 273/185 |
| 5,245,862 A | 9/1993 | Zeiss ............................. 73/79 |
| 5,419,565 A | 5/1995 | Gordon et al. .............. 273/374 |
| 5,437,457 A | 8/1995 | Curchod ..................... 273/185 |
| 5,575,719 A | 11/1996 | Gobush et al. ............. 473/223 |
| 5,626,526 A | 5/1997 | Pao et al. .................... 473/156 |
| 5,672,809 A | 9/1997 | Brandt ....................... 73/12.01 |
| 5,846,139 A | 12/1998 | Bair et al. .................. 473/156 |
| 5,863,255 A | 1/1999 | Mack .......................... 473/152 |
| 6,385,559 B2 | 5/2002 | Boehm ....................... 473/223 |
| 6,527,648 B2 * | 3/2003 | Erickson et al. ............ 473/221 |
| 6,602,144 B2 * | 8/2003 | Manwaring et al. ........ 473/198 |

OTHER PUBLICATIONS

U.S. patent application Ser. No. 09/379,592 filed Aug. 24, 1999 entitled "Multishutter Camera System".

* cited by examiner

Primary Examiner—Max Noori
(74) Attorney, Agent, or Firm—Swidler Berlin Shereff Friedman, LLP

(57) ABSTRACT

The present invention comprises an automated machine for testing the physical properties of spherical objects. Preferably, the apparatus comprises a firing mechanism that includes an inner and outer barrel. An object inside the firing mechanism is propelled towards a striking surface that faces the firing mechanism. Two sensors located at predetermined points between the firing mechanism and the striking surface measure the inbound and outbound velocity of the object. A computing device then uses an algorithm to determine the COR of a given set of objects. An angular device uses gravity to direct the objects to a retrieval chute, which uses a tubing system to direct the objects for re-testing or collection.

26 Claims, 15 Drawing Sheets

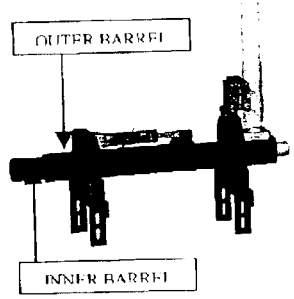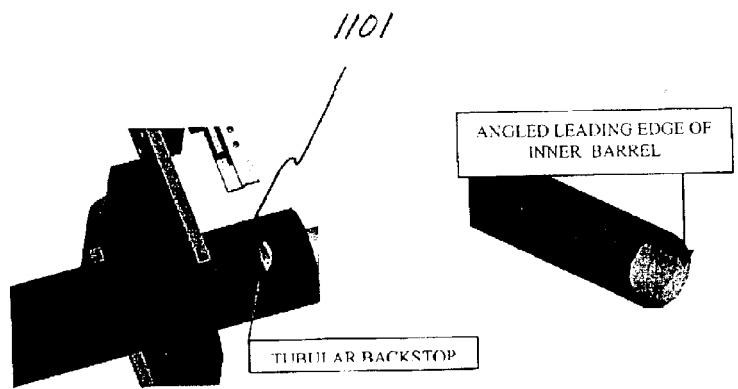
Fig. 11a      Fig. 11b      Fig. 11c

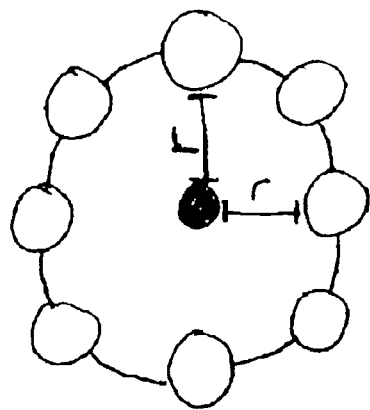
Fig. 13a
Fig. 13b
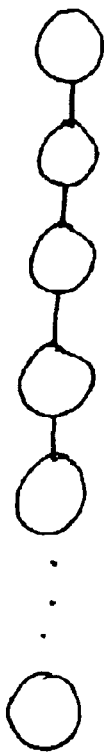
Fig. 13c
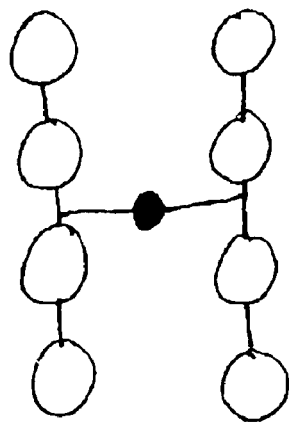

GOLF BALL COR TESTING MACHINE

CROSS-REFERENCE TO RELATED APPLICATIONS

This application is a continuation-in-part of U.S. patent application Ser. No. 09/955,124 filed Sep. 19, 2001 ("Apparatus and Method for Measurement of Coefficient of Restitution and Contact Time"), now U.S. Pat. No. 6,571,600.

FIELD OF THE INVENTION

The present invention relates to an apparatus for testing spherical objects. More specifically, the present invention relate to an apparatus for testing the physical properties, Coefficient of Restitution, and quality of golf balls.

BACKGROUND OF THE INVENTION

Various types of equipment have been used for testing the physical properties of objects such as golf balls. One type of equipment employs a mechanical device that is programmed to swing a golf club in a repeated pattern to drive balls from a fixed tee position in order to test for travel distances of the balls. Other types of equipment use a propelling mechanism to launch a ball through a predetermined path, along which sensors are provided for recording the flight of the ball.

One such device employs a barrel into which a golf ball can be mounted via a hinged cover in the side of the barrel. This type of device uses a sealing ring within the bore of the barrel to hold the ball in position. After closing the hinged cover, a pneumatic charge is delivered to the barrel so as to push the ball through the sealing ring, and out of the barrel, at a high speed. However, this type of mechanism is not able to consistently launch balls at a given velocity. This is typically due to the fact that the threshold for passing the ball through the sealing ring varies for each ball being fired. Typically, this causes an inconsistency from between ½ to 2 feet/second. Because the sealing ring causes an inconsistency in the velocity of the ball, it becomes difficult to adjust the velocity of the ball to test at different speeds. When testing velocity dependant physical characteristics, such as Coefficient of Restitution, this is often desirable.

When measuring the characteristics of a ball, it is desirable to propel the ball at a known and consistent velocity. This can be important when measuring many ball characteristics, such as distance, coefficient of restitution, durability, or quality testing. Specifically, when testing coefficient of restitution, it is particularly important to be able to propel a set of balls at a consistent velocity.

Current devices have many other drawbacks. These devices are typically bulky, and require many components. In addition, the devices typically require balls to be manually fed and recovered, resulting in significant downtime and increased operator time. Additionally, current devices do not provide a reliable apparatus or method for testing at different ball velocities. Furthermore, existing devices do not conveniently allow for the testing of differently sized balls.

A continuing need exists for an apparatus for accurately testing the physical properties of golf balls while minimizing the time and number of components required.

SUMMARY OF THE INVENTION

In a preferred embodiment, the present invention comprises an apparatus for measuring the physical properties of a golf ball. The apparatus comprises a striking surface, and a propelling device facing the striking surface. The propelling device preferably fires a golf ball towards the striking surface. In a preferred embodiment, the propelling device comprises an interchangeable barrel system. A sensing unit is located between the striking surface and the propelling device. The sensing unit preferably has a measuring field covering a space between the propelling device and the striking surface. Preferably, the sensing unit is capable of measuring the time it takes for the golf ball to travel a distance in the measuring field of the sensing unit. A computing unit is communication with the sensing unit, and is preferably capable of calculating the Coefficient of Restitution of the golf ball.

In a preferred embodiment, the interchangeable barrel system comprises an inner barrel and an outer barrel. The inner barrel has a sliding connection with the outer barrel, and is preferably interchangeable based on the size of the golf ball being fired. The outer barrel preferably has an opening that allows a golf ball to be loaded into the barrel system.

A golf ball is loaded into the barrel system by inserting a golf ball through the opening in the outer barrel. The inner barrel, which has an angled leading edge, then captures the ball with the assistance of a tubular backstop that is attached to the outer barrel. The leading edge of the inner barrel preferably has an angle of between 30 and 50 degrees.

In a preferred embodiment, the diameter of the inner barrel is between about 0.038 and 0.042 inches greater than the diameter of the golf ball. The diameter of the outer barrel is between about 0.030 and 0.050 inches greater than the diameter of the inner barrel.

In a preferred embodiment, the entire barrel system is positioned at an angle relative to a horizontal plane. The angle is preferably chosen to prevent the golf ball from falling out of the barrel system. In a preferred embodiment, this angle is preferably between 0.01 and 3.0 degrees.

In a preferred embodiment, the barrel system and the striking surface are positioned at an angle that is not orthogonal. The angle is preferably determined in order to prevent a fired golf ball from re-entering the barrel system after rebounding off of the striking surface. In a preferred embodiment, the angle between the propelling device and the striking surface is between 90 and 95 degrees.

Preferably, the barrel system includes a fast acting valve that closes substantially as soon as the golf ball leaves the barrel system. This prevents a propellant from affecting the flight path of the ball or, in some embodiments, the sensing unit.

In a preferred embodiment, the sensing unit comprises at least two sensors. One of the sensors may be placed substantially close to the striking surface in order to calculate the impact duration between the golf ball and the striking surface.

The fired golf balls are collected using a chamber floor that employs gravity to direct the balls towards an exit chute. The exit chute directs the balls towards a pneumatically controlled return system. The return system has a valve that either directs balls back to the barrel system, or to a collection device.

The present invention also comprises a method of measuring the Coefficient of Restitution (COR) of a plurality of golf balls. The method includes providing a propelling device, a striking surface, and a sensing unit located between the striking surface and then propelling device. Golf balls are first fired from the propelling device towards the striking surface. Once the balls are fired, the sensing unit measures the velocity of the balls before it contacts the striking surface. The sensing unit then measures the velocity of the balls after it rebounds from the striking surface. Any desired method may then be used to determine the COR of the golf ball.

In a preferred embodiment, the method also includes collecting the fired golf balls after they rebound from the striking surface. The balls may then be redirected to either the propelling device or a collection device. If the balls are directed towards the propelling device, they are once again fired and their velocities are measured both before and after contacting the striking surface. In another embodiment, the contact time of the golf ball may be determined using a substantially similar method.

Other and further aspects of the present invention will be apparent from the following description and claims and are illustrated in the accompanying drawings, which by way of illustration, show preferred embodiments of the present invention. Other embodiments of the invention embodying the same or equivalent principles may be used and structural changes may be made as desired by those skilled in the art without departing from the present invention and the purview of the appended claims.

BRIEF DESCRIPTION OF THE DRAWINGS

The objects and advantages of the present invention will be better understood and more readily apparent when considered in conjunction with the following detailed description and accompanying drawings which illustrate, by way of example, preferred embodiments of the invention and in which:

FIGS. 11a–c are diagrams showing exemplary inner and outer barrels according to the present invention.

FIGS. 13a–c are diagrams showing exemplary barrel arrangements according to the present invention.

DETAILED DESCRIPTION OF THE DRAWINGS

Figure 1:
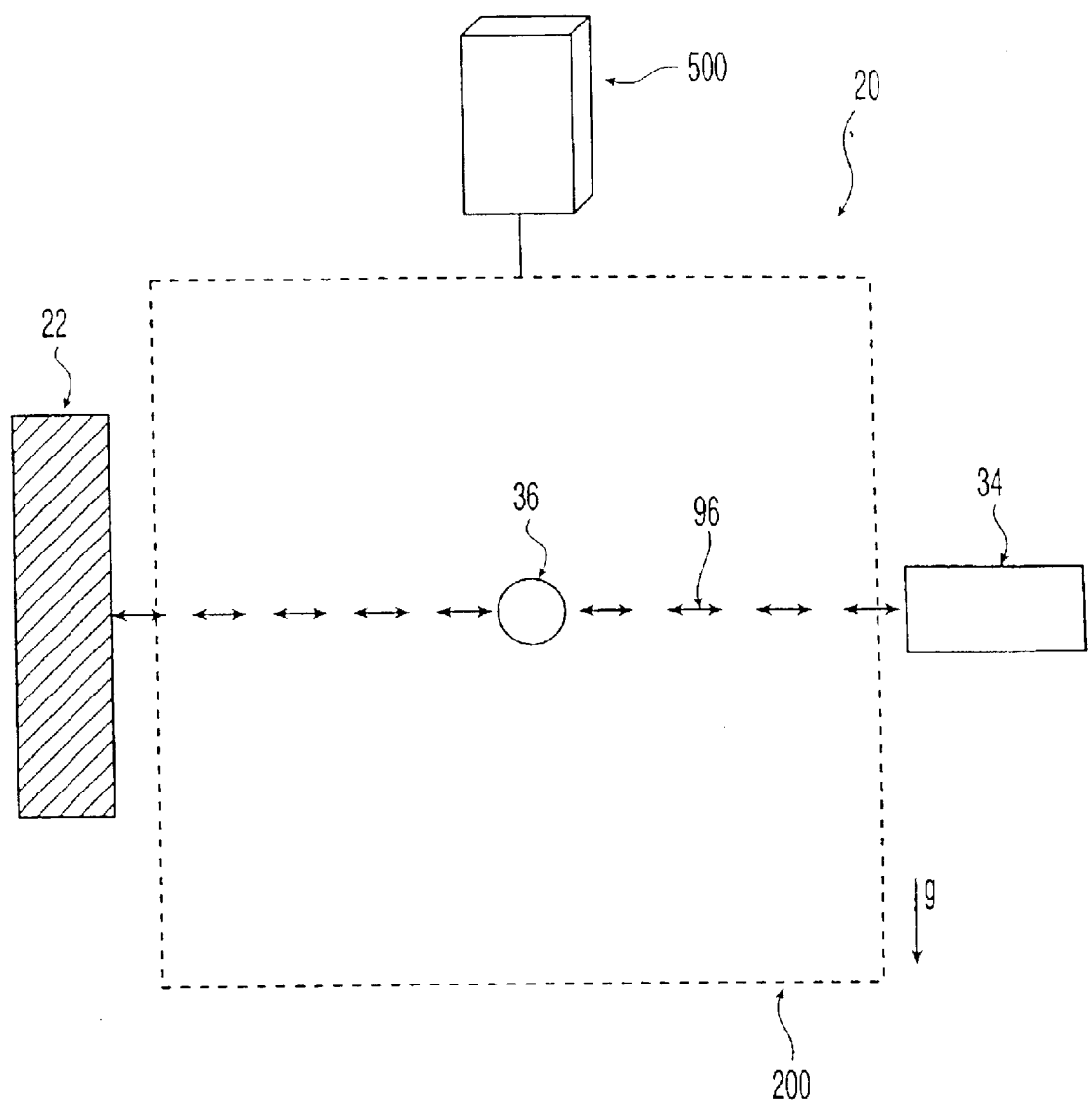
FIG. 1 is an arrangement of the apparatus of the present invention.

In an exemplary embodiment, the present invention relates to an automated machine used to test spherical objects. The properties that may be tested include physical properties, for example, quality, durability, and Coefficient of Restitution (COR) of spheres.

In a preferred embodiment, substantially all of the functions of the present invention may be automated. The capabilities of the present invention include, for example, the ability to load, fire, and return one or more balls through a testing apparatus. Additional capabilities may be added to the present invention according to a desired application.

The present invention relates to an apparatus and method for determining the COR of a spherical object. In a preferred embodiment, the spherical object may be a golf ball or golf ball core. In a preferred embodiment, the present invention provides an apparatus that automatically tests and collects a desired number of golf balls.

In a preferred embodiment, the present invention comprises a ball return tubing system 901, a firing barrel 903, a testing chamber 905, a striking surface, and a ball retrieval mechanism. In a preferred embodiment, the present invention also comprises at least two sensors located within the testing chamber 905, a pressurized air tank 911, a loading cylinder 913, a computer 915, and a set of differently sized firing barrels 917.

According to the present invention, a desired number of golf balls may be loaded into a ball return tubing system 901. The ball return tubing system 901 carries the balls into a loading cylinder 913. The loading cylinder 913 is capable of feeding the balls into a firing barrel 903. Once a ball is loaded into the firing barrel 903, pressurized air from the pressurized air tank 911 is used to fire the ball at the striking surface, through the testing chamber 905. The striking surface (not visible in FIG. 9), is located within the testing chamber 905, on the end opposite the firing barrel 903. The ball will eventually fall to the floor of the testing chamber 905 after rebounding off of the striking surface. Using a ball retrieval mechanism located on the floor of the testing chamber 905, the balls are fed back into the ball return tubing system 901. The controllable gate 907 may be used to either feed the balls back into the firing barrel 903, or to direct the balls to a pick-up tray 909.

In a preferred embodiment, the present invention may determine the COR of the tested balls based on at least two sensors that may be located at predetermined points between the firing barrel 903 and the striking surface. The sensors measure the inbound and outbound velocities of each fired ball. The sensors send this and other information to a computer 915, which may then be used to determine the COR. In a preferred embodiment, differently sized balls may be tested by replacing an existing firing barrel 903 with one of the differently sized firing barrels 917.

The spherical objects that may be tested include golf balls, golf ball cores, or other golf ball components. The spherical object may also include a golf ball that is not completely formed, for example, a golf ball without a cover. However, the present invention is not intended to be limited to golf balls or golf ball cores. Any type of spherical object, for example, tennis balls, racquet balls, basketballs, volleyballs, etc., may be used. As will be appreciated by those skilled in the art, the physical properties of any type of spherical object may be tested in accordance with the present invention.

According to the present invention, one or more balls may be loaded into a transport system. In a preferred embodiment, the transport system comprises a ball return tubing system 901 that may be used to transport the balls to a loading cylinder 913. In alternate embodiments, any transport system capable of moving spherical objects from one point to another may be used.

Figure 10:
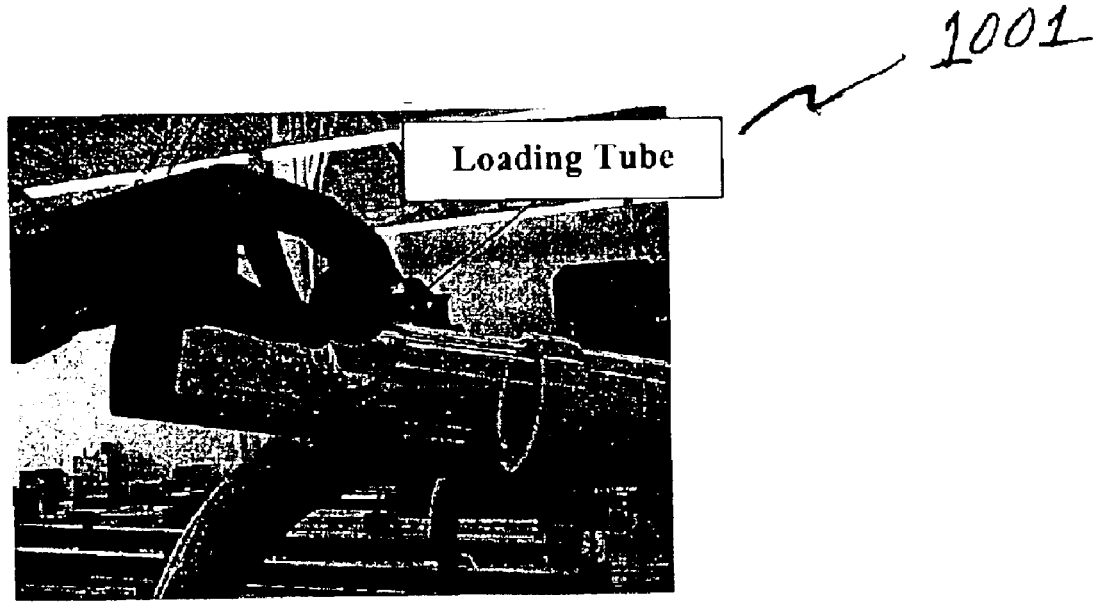
FIG. 10 is a diagram showing an exemplary loading tube according to the present invention.

In a preferred embodiment, a desired number of balls may be loaded into the ball return tubing system 901 via a loading tube 1001, shown in FIG. 10. The tubing system 901 carries the balls to the loading cylinder 913. The ball return tubing system 901 ends at the loading cylinder 913, and begins again at the floor of the testing chamber 905. Using gravity, balls that exit the testing chamber 905 may be fed back to the firing barrel 903 or they may be fed to a pick up tray 909. The destination of the balls may be controlled using a controllable gate 907. In some embodiments, the gate 907 may be controlled manually. In other embodiments, the gate 907 may be controlled automatically, for example, by using a computer 915 or controller.

According to the present invention, the loading cylinder 913 receives balls that are loaded into the loading tube 1001. In a preferred embodiment, the loading cylinder 913 comprises a plurality of pneumatically operated fingers which control ball feed into a firing barrel 903. In this embodiment, the pneumatically operated fingers separate the balls from one another. Each ball may then be fed into the firing barrel 903 individually. While a selected ball is being fed into the firing barrel 903, the pneumatically operated fingers prevent any other balls from entering. In a preferred embodiment of the present invention, the pneumatic fingers may be controlled through the use of a computer 915 or a controller. In other embodiments, the pneumatic fingers may be controlled manually. Other types of loading systems may be employed in alternate embodiments. Alternate loading systems may use any ball feed control mechanism that is known to those skilled in the art.

In a preferred embodiment, the loading cylinder 913 is connected to the firing barrel 903. However, in alternate embodiments, intermediate apparatus may be placed in between the loading cylinder 913 and the firing barrel 903. In alternate embodiments, the firing barrel 903 may be replaced by any type of device that is capable of propelling an object towards a striking surface. These devices include, for example, an air cannon, a linear motor, and a translating belt.

In a preferred embodiment according to the present invention, the firing barrel 903 comprises a shuttling barrel system used for positioning and firing balls. According to this embodiment, the firing barrel 903 comprises an inner and outer barrel, as shown in FIG. 11a. Preferably, the outer barrel is located in a fixed position and has a fixed diameter.

The diameter of the outer barrel may be chosen based on the size of the balls that are going to be tested. The inner barrel may be attached to the outer barrel using a variety of methods, such as a slip fit mechanism. Preferably, the two barrels fit together snugly and allow objects to be fired repeatedly. When clearance between the two barrels is too small, friction forces may restrict the movement of the inner barrel. When the clearance is too large, air that is intended to be forced into the inner barrel may flow between the two barrels. Preferably, the clearance between the two barrels is chosen to minimize both of these undesirable effects. In a preferred embodiment, when the clearance is less than approximately 0.020", the friction between the barrels may impact the spin of the fired ball. In addition, the velocity of the fired ball may be inconsistent. When the clearance between the two barrels is larger than 0.060", turbulence may adversely affect the firing of the ball.

Preferably, the diameter of the outer barrel is between 0.025 and 0.075" greater than the diameter of the inner barrel. More preferably, the clearance between the outer barrel is between 0.030 and 0.050" greater than the diameter of the inner barrel. Most preferably, the clearance is between 0.035 and 0.045". Inner barrels may also be chosen based on the diameter of the object to be tested. In a preferred embodiment, the inner diameter of the inner barrel is between 0.030 and 0.050" greater than the diameter of the ball. More preferably, the diameter of the inner barrel is between 0.038 and 0.042" greater than the diameter of the ball.

In a preferred embodiment, balls are loaded into the barrel system as shown in FIG. 11b, using, for example, an entryway 1101 in the outer barrel. The inner barrel has, for example, an angled leading edge that captures the ball and places it into the proper firing position, as shown in FIG. 11c. Once the ball is loaded into the outer barrel, the inner barrel moves towards the tubular backstop shown in FIG. 11b. In a preferred embodiment, the tubular backstop is fixed to the outer barrel, and provides a shuttling mechanism into the barrel. The ball rests against the tubular backstop and cooperates with the leading edge of the inner barrel to position the ball inside the inner barrel. Preferably, the diameter of the tubular backstop is smaller than the diameter of the smallest ball or component that needs to be fired. More preferably, the tubular backstop is between 0.030 and 0.050" smaller than the diameter of the ball. The tubular backstop may be manually changed according to the size of the ball being tested.

In a preferred embodiment, the ball should be positioned so that it is completely inside the inner barrel, as shown in FIG. 11d. Preferably, the length of the leading edge is less than or equal to the radius of the ball. This allows the ball to be properly positioned inside the inner diameter of the barrel. When the length of the leading edge is larger than the radius of the ball, the ball may be positioned improperly, as shown in FIG. 11e. This may prevent the ball from being fired properly. Preferably, the leading edge has an angle between 10 and 80 degrees. More preferably, the leading edge has an angle between 30 and 50 degrees.

Using its leading edge, the inner barrel captures the ball. The inner barrel may then provide a smooth, continuous barrel for the ball to be propelled out of. Typically, it is difficult to accurately, and repeatedly fire a ball at a desired velocity. However, the smooth, continuous, closed surface of the inner barrel allows the ball to be precisely and accurately propelled at a desired velocity.

Figure 9:
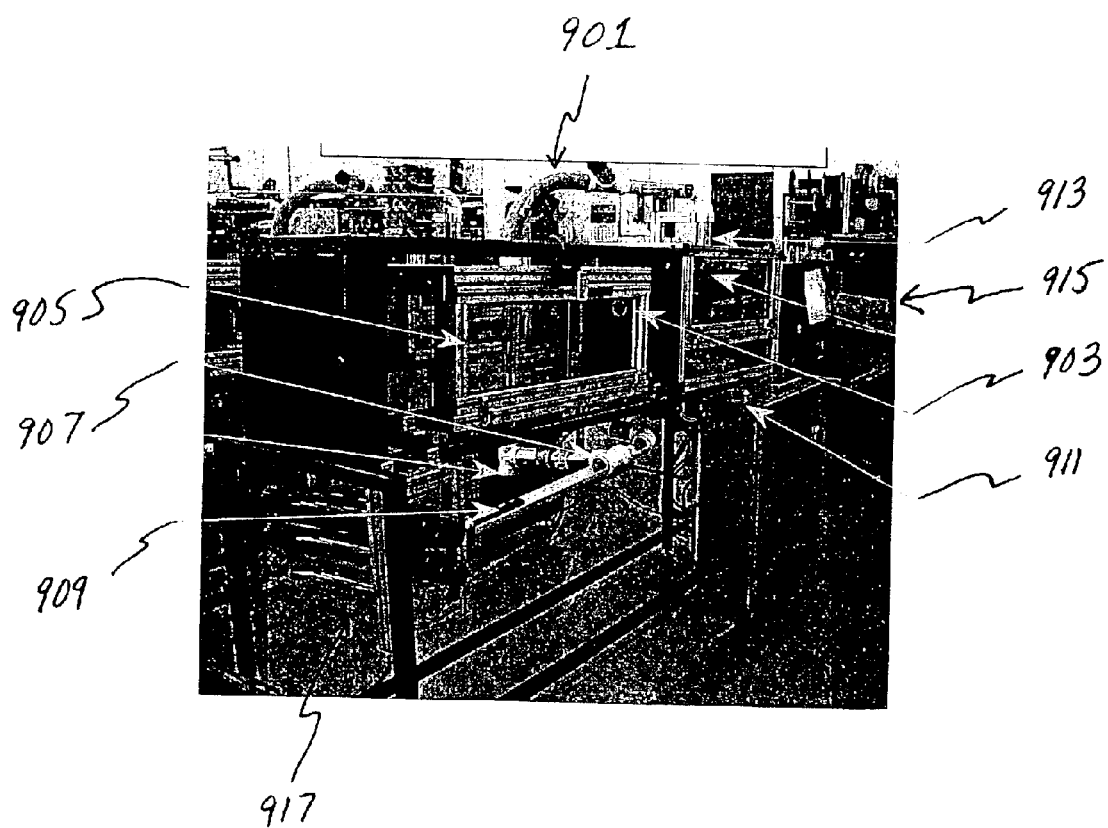
FIG. 9 is a diagram showing an overview of a preferred embodiment of the present invention.

According to the present invention, the size of the spherical objects may be varied as desired. In order to accommodate differently sized objects, the inner barrel of the firing barrel 903 may be interchanged. In a preferred embodiment, the alternate firing barrels 917 are stored as shown in FIG. 9. In a preferred embodiment, the differently sized firing barrels 917 of the present invention may be manually interchanged. Firing barrels may be interchanged based on, for example, selective use of alignment mechanisms and fasteners. Alignment pins, for example, clevis pins or screws, may be used with fasteners to detach and attach barrels. More preferably, a single thumb screw may be used to detach and attach barrels.

Figures 12A, 12B:
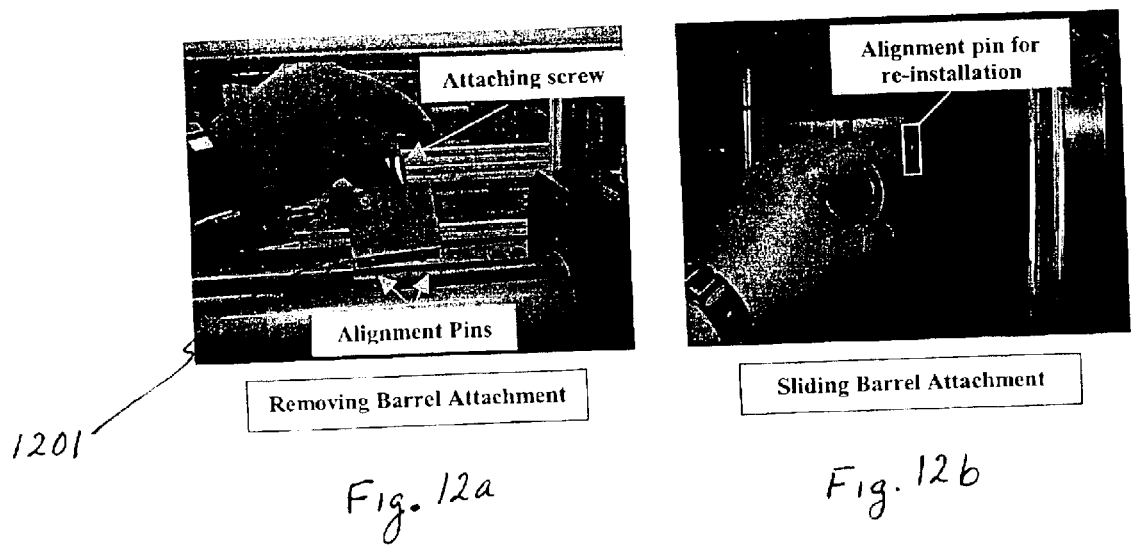
FIGS. 12a–b are diagrams showing an exemplary screw and alignment pins according to the present invention.

According to the present invention, each inner barrel has at least one alignment pin attached to it. In a preferred embodiment, two alignment pins attached to the inner barrel aid in attaching a piston 1201 to the inner barrel, as shown in FIG. 12*a*. In a preferred embodiment, the piston 1201 allows the inner barrel to move back and forth within the outer barrel. This motion is necessary, for example, to allow the inner barrel to capture a ball, as previously described with respect to FIGS. 11*b–e*. Once the pneumatic device 1201 is aligned with the inner barrel, an attaching screw may be used to hold the piston 1201 in place.

In a preferred embodiment, an alignment pin also aids in the insertion of the inner barrel. As shown in FIG. 12*b*, an alignment pin on the inner barrel corresponds to a groove on the inner circumference of the outer barrel. When matched with the groove, the alignment pins simplify the insertion of the inner barrel into the outer barrel. This is just one example of how the inner and outer barrels may be aligned and inserted. In other embodiments, any method or apparatus known to those skilled in the art may be used to facilitate the insertion of the inner barrel into the outer barrel.

In a preferred embodiment, the firing barrel 903 is set at an upward angle. The upward angle may be varied to allow gravity to keep the ball from rolling out of the barrel 903. Preferably, the barrel 903 angle in relation to level ground is between 0.01 and 60 degrees. More preferably, the angle is between 0.01 and 3.0 degrees. In some embodiments, the entire testing chamber 905 may be placed at an angle with respect to the ground. In such alternate embodiments, the ball may be prevented from rolling out of the barrel 903 using, for example, a stopping mechanism. This may be necessary in applications where, for example, a ball is fired towards a target at an angle that is less than 90 degrees with respect to the ground.

In an exemplary embodiment, the firing barrel 903 may be interchanged automatically. In this embodiment, a plurality of firing barrels are placed in desired configurations. In one such embodiment, shown in FIG. 13*a*, a plurality of firing barrels may be placed in a substantially circular manner at a given radius from a central point. In this embodiment, the firing barrels may be interchanged by rotating the substantially circular arrangement. In this way, differently sized balls may be fired from the present invention while minimizing the time required to replaced differently sized firing barrels. In this embodiment, the firing barrels may be interchanged automatically using automatic switching, for example, through the use of an electric motor. The switching may be controlled by a user, or alternately, through the use of a computer 915 or controller.

In an alternate embodiment shown in FIG. 13*b*, a predetermined number of differently sized firing barrels may be placed substantially adjacent to each other in a substantially linear manner. In this embodiment, firing barrels capable of accommodating differently sized spheres may be interchangeable by moving the desired firing barrel into place. In another embodiment, shown in FIG. 13*c*, two sets of substantially adjacent firing barrels, located in a substantially linear manner, may be used to alternate the size of the firing barrel. The substantially linearly arranged firing barrels may be arranged at any angle with respect to the ground. As will be appreciated by those skilled in the art, the arrangement of differently sized firing barrels may be changed in according to a particular application.

Figure 14:
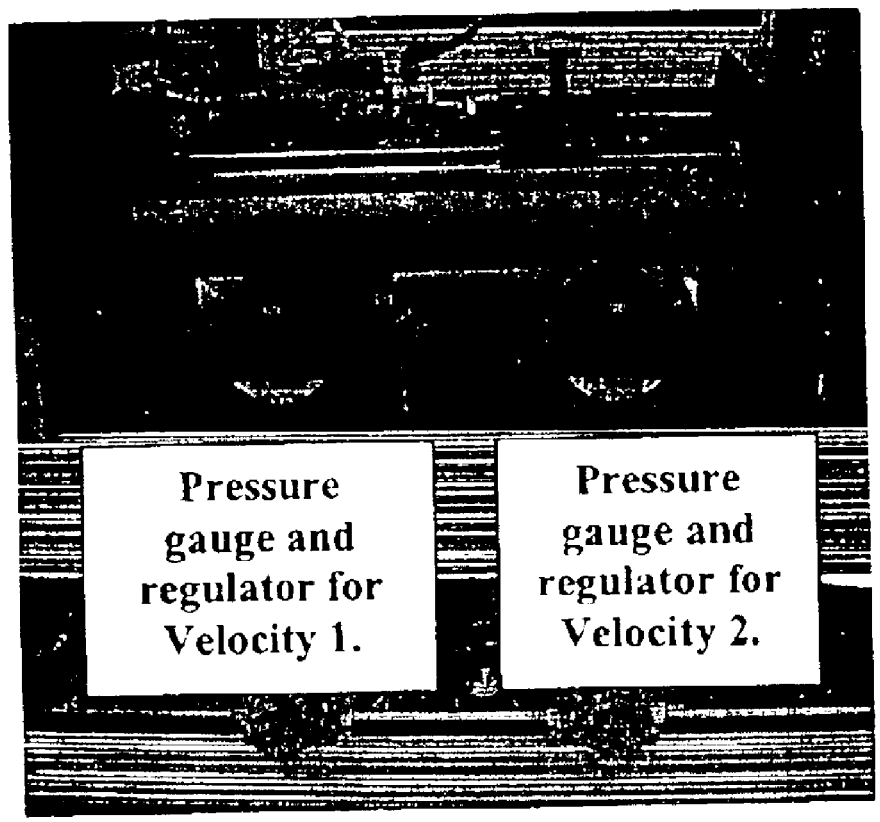
FIG. 14 is a diagram showing exemplary pressure gauges and regulators according to the present invention.

In a preferred embodiment, balls may be fired out of the firing barrel 903 by pneumatically firing pressurized air into the firing barrel 903, propelling the ball into flight. In a preferred embodiment, the pressurized air is stored in a pressurized air tank 911. The volume of the air tank 911 is preferably, for example, at least 1 time the volume of the inner barrel. More preferably, the volume of the tank 911 is between 3 to 5 times the volume of the inner barrel. Most preferably, the volume of the tank 911 is between 8 to 11 times the volume of the inner barrel. The pressure that is fired into the firing barrel 903 may be monitored and adjusted by using one or more pressure gauges and regulators, as shown in FIG. 14. It is sometimes desirable to determine the COR of a ball based on measurements determined at two separate velocities. In these applications, a second pressure gauge and regulator may be desirable. In other embodiments, alternate devices such as a regulated air supply, may be used to fire air into the inner barrel.

In a preferred embodiment, the firing barrel 903 is capable of propelling a ball at speeds from about 80 to about 180 feet/second (ft/s). However, the pressure may be adjusted to fire the ball at any desired speed. In other embodiments, the air may be generated by any type of pressurized air mechanism known to those skilled in the art.

In a preferred embodiment, the pressurized air is fired into the firing barrel 903 for a predetermined time period. This time period may be chosen so that the ball can be propelled at a desired velocity. After this time period expires, a fast acting cut-off valve, for example, a sinclair valve, stops the pressurized air from being fired into the firing barrel 903. In a preferred embodiment, the fast acting valve has a repeatable opening time. Preferably, the fast acting valve should provide a good seal at low and high pressures.

In a preferred embodiment, the pressurized air stream should last until the ball leaves the barrel. It is desirable to discontinue the pressurized air stream immediately after the ball leaves the barrel. This prevents the air from affecting the velocity of the ball after it has left the tube. Additionally, certain types of sensors, for example, light gates sensors, may be affected by high pressure air streams. The fast acting cut-off valve ensures that the pressurized air stream is only fired into the firing barrel 903 long enough to propel the ball, but not so long that it may affect other parts of the present invention. Preferably, the volume of air fired into the inner barrel is 4 times the volume of the inner barrel. More preferably, the volume of air fired into the inner barrel is twice the volume of the inner barrel. Most preferably, the volume of air fired into the inner barrel is equal to the volume of the inner barrel.

In a preferred embodiment, the ball leaves the firing barrel 903 and imparts to an immovable plate. Preferably, the immovable plate is a non-deformable plate. The plate may be formed out of any type of material, for example, a metal, an alloy, plastic, or a combination of other materials known to those skilled in the art. In a preferred embodiment, the immovable plate is located at an angle with respect to the firing barrel 903. Preferably, the angle between the barrel 903 and the plate is close to 90 degrees to avoid placing spin on the rebounding object. However, the angle should be chosen so that the ball is prevented from rebounding off of the immovable plate and re-entering the barrel 903. Preferably, the angle of the immovable plate with respect to the firing barrel 903 is between 45 and 135 degrees. More preferably, the angle is between 90 and 95 degrees. Most preferably, the angle is between 90.5 and 92 degrees.

In other embodiments, the ball may be prevented from re-entering the barrel 903 using alternate methods. For example, the barrel 903 may be placed at an angle, in a horizontal direction, with respect to the immovable plate. In such an embodiment, the angle should be chosen so that the ball is able to rebound off of the immovable plate and pass through the sensors. The angle should not be so large that the ball rebounds off the immovable plate and hits the side of the testing chamber 905. The horizontal angle of the barrel 903 with respect to the immovable plate is preferably close to zero degrees to avoid placing spin on the rebounding object. Preferably, the horizontal angle is between 0 and 10 degrees. More preferably, the horizontal angle is between 0 and 5 degrees. Most preferably, the horizontal angle is between 0 and 2 degrees.

The testing chamber 905 may be formed out of any material or materials. In a preferred embodiment, the chamber 905 is a rectangular cube. However, the testing chamber may have any shape. In a preferred embodiment, the volume of the chamber 905 is sufficient to enclose the immovable plate and other desired hardware. Preferably, the testing chamber 905 prevents any outside interference from affecting the firing barrel 903, the ball, and the immovable plate.

In a preferred embodiment, the floor of the testing chamber 905 includes a ball retrieval mechanism. In this embodiment, the floor of the chamber 905 is angled. Preferably, the angle of the floor is sufficient to allow gravity to provide ball motion towards an exit chute. The angle of the floor or machine may be, for example, between 0 and 90 degrees. More preferably the angle may be between 1 and 5 degrees. The exit chute may be located at any point on the chamber 905 floor. In a preferred embodiment, the exit chute is connected to the tubing system 901. Depending on a particular application, the balls may either be returned to be fired at, for example, a second velocity, or they may be exited for collection. As will be appreciated by those skilled in the art, any ball collection apparatus or method may be used in accordance with the present invention.

Once the ball is fired from the firing barrel 903, it passes through the air at an outbound velocity, and strikes the immovable plate. The ball then rebounds off of the plate at an inbound velocity. In the preferred embodiment, the inbound and outbound velocity may be measured using, for example, a minimum of two sensors. The sensors may be separated by a desired distance in order to detect the velocity of the fired object.

Figure 15A:
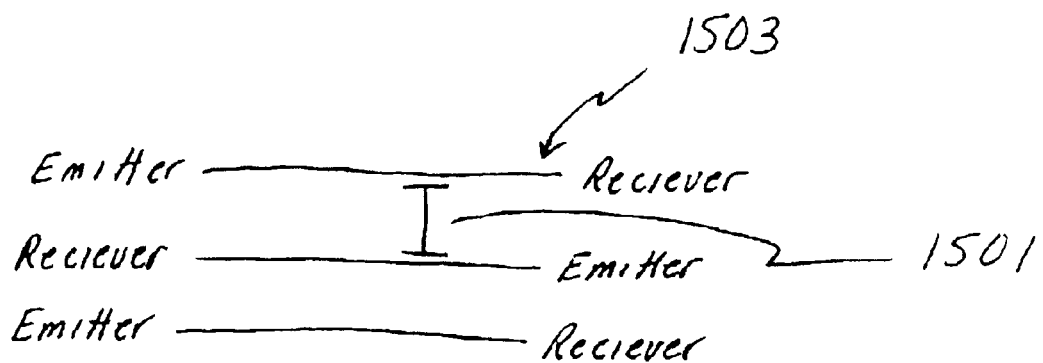
FIGS. 15a–b are diagrams showing exemplary arrangements of emitters and receivers according to the present invention.
Figure 15B:
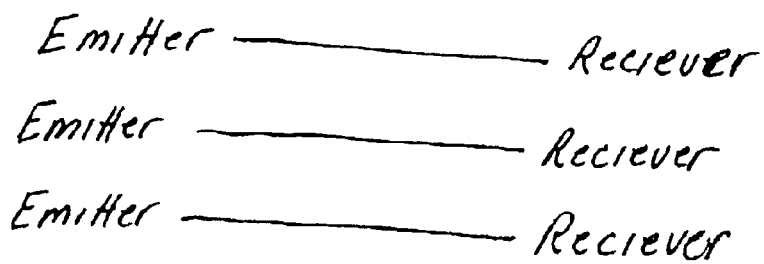

In a preferred embodiment, the sensors may have LED's or light emitting devices and receiving lenses. More preferably, the sensors are infrared LED through beam sensors. Infrared LED sensors typically have a long life span, require less maintenance, and are more accurate when used to detect low speed objects, such as a golf ball. The sensors may be arranged in any manner to allow sensing of an object passing through a predetermined plane. In a preferred embodiment, an alternating linear array of individual emitters and receivers may be arranged opposite a similar alternating linear array of individual receivers and emitters, as shown in FIG. 15a. Typically, corresponding emitters and receivers may differ in size. Alternately stacking emitters and receivers allows the distance 1501 between the beams 1503 to be minimized. In other embodiments, the linear array of emitters may be arranged opposite a linear array of individual receivers, as shown in FIG. 15b.

In a preferred embodiment, the distance between the emitters and receivers may be, for example, between 1/16 and 1/2 inches. More preferably, the distance between the sensors may be, for example, between 1/8 and 1/4 inches. In other embodiments, any type of sensors known to those skilled in the art may be used. Sensors that may be used include, for example, a light gate, a ballistics screen, an optical sensor, or the like. The type of sensor used should be suitable for detecting low speed objects. Preferably, the position of the sensors should be well known, i.e., they should be placed at precise distances from the firing barrel.

After the ball is fired from the firing barrel 903, it is detected by each of the two sensors. The ball then imparts to the immovable plate, rebounds off of the plate, and is detected by the sensors again. The sensors precisely detect the passage of the ball. Using the recorded inbound and outbound times of ball passage, along with the known precise sensor locations, inbound and outbound velocities may be calculated. In a preferred embodiment, the sensors are connected to a computer 915 or controller. The computer 915 or controller analyzes the times that are relayed from the sensors and calculates the inbound and outbound velocities. The COR of a ball may be calculated because the COR is the ratio of the outbound velocity to the inbound velocity.

The relationship between COR and ball velocity varies in a substantially linear manner. The most reliable method of determining the COR of a given set of balls is to test the balls at two substantially different velocities. A graph may then be created using a slope of velocity vs. COR. COR values at any intercept of this slope may then be extracted. This method of calculating COR is well known to those skilled in the art.

Preferably, the two velocities are generated by using two pressures. This may include determining the COR at a low pressure, for example, 80 feet/second (ft/s), and at a high pressure, for example, 180 ft/s. As previously discussed, the pressures may be generated by using a pressurized air tank 911 or a air pressure regulator or regulators. This method is well known to those skilled in the art.

In alternate embodiments, the present invention may be used to test, for example, the quality or durability of an object. In such embodiments, a sphere may be fired at an immovable plate, as previously described. For example, it may be desirable to determine a balls' durability when it is struck by a club at a given velocity. By firing the ball at an immovable plate, recording the balls inbound and outbound velocity, and then collecting the ball for analysis, the durability of a ball may be determined. This is just one example. Any type of physical analysis of a spherical object desired by those skilled in the art may be determined in accordance with the present invention.

In a preferred embodiment, one or more balls are loaded into a loading cylinder 913. The loading cylinder 913 then individually feeds each ball into the firing barrel 903. Differently sized firing barrels 917 may be used depending on the size of the object that is being fired. A pressurized air tank 911 then fires air into the firing barrel 903, causing the ball to be propelled out of the barrel and into a testing chamber 905. As the ball passes through the testing chamber 905, two sensors precisely detect the passage of the ball. The sensors may transmit this information to a computer 915 or controller that records the information.

After passing through the sensors, the ball imparts on a striking surface, and rebounds off of it. After rebounding, the ball once again passes through the two sensors. The passage of the ball is once again precisely recorded and transmitted to a computer 915 or controller. This process is repeated for each ball that needs to be tested.

After a ball rebounds off the striking surface, it eventually comes to rest on the floor of the testing chamber 905. The floor of the testing chamber uses gravity to direct the balls towards a ball retrieval mechanism that is located on the floor of the testing chamber 905. The ball retrieval mechanism then directs the balls into a ball return tubing system 901. A controllable gate 907 directs the balls once they enter the ball return tubing system 901. If it is desirable to re-test the balls, they may be directed to continue along the ball return tubing system 901. If it is desirable to collect the balls, the controllable gate 907 may direct the balls to a pick up tray 909. If the balls are directed back along the ball return tubing system 901, they will be directed back towards the firing barrel 903 for re-testing. The process may then be repeated.

In a preferred embodiment, a computer 915 or controller may be used to control each aspect of the invention. For example, the computer 915 or controller may control the pressurized air tank 911, the controllable gate 907, or the loading cylinder 913. In addition, the computer 915 or controller may calculate the COR of one or more balls based on the data transmitted from the sensors. Of course, this is just one example. The operation of the present invention may be modified, and steps may be added, removed, or rearranged, as desired by those skilled in the art.

Other embodiments of the present invention are directed towards an apparatus and method for the simultaneous measurement of contact time and COR of a golf ball or golf ball core during normal use. This aspect of the invention may be used interchangeably with other embodiments described herein, including those described above.

One embodiment of the invention, shown in FIG. 1, includes an apparatus 20 having an object 36, a propelling device 34, a striking surface 22, at least one sensing unit 200, and a computing unit 500 in communication with the sensing unit.

The object 36 can be any item that is able to be fired from the propelling device 34, for example, such as a golf ball or a golf ball core. The propelling device 34 can be any device that can propel the object toward the striking surface 22, for example, such as an air cannon, a linear motor, a translating belt, or the like. The propelling device 34 is preferably capable of propelling the object 36 at speeds from about 80 to about 180 feet/second (ft/s). In one embodiment, the propelling device 34 is an air cannon that propels the object 36 initially horizontally in the air toward the striking surface 22.

The line pressure (about 80 psi to about 90 psi) may enter a regulator in order to reduce the pressure in the air cannon to between about 40 psi to about 50 psi. In one embodiment, the air is stored in a tank (not shown). The tank can hold a volume of air, for example, about 80 cubic inches to about 90 cubic inches. A solenoid, e.g., such as a Mac Solenoid valve Model #56C-13-611JM, may be used to trigger a valve in order to release the stored pressurized air. An industrial valve, e.g., such as a Dubbin Industrial Valve C244 5001, may be used to release air into the main firing chamber to propel the object.

The firing pressure is controlled by a regulator, e.g., such as a Fairchild Regulator Model #10. The object velocity can be varied by varying the pressure with the regulator. As the object 36 is released from propelling device 34, it passes through at least one sensing device 30.

The sensing unit(s) 200 includes sensing devices which, in turn, include sensors capable of detecting passing objects. Suitable sensing devices may be obtained from Ordnance Industries, Model #6100 Solid State Ballistics Screens.

The computing unit 500 includes timers and a central processing unit (CPU), and is in communication with the sensing unit 200. The computing unit 500 can register the detection made by the sensing unit(s) 200 and can then calculate the physical response of the object 36 based on those detection measurements and other necessary information. Extra features, such as safety mechanisms and release plates, are preferably added to make the device easier and safer to use. A programmable logic controller (PLC), e.g., a Direct Logic 305 unit, may be used to automate operation.

In one embodiment, the striking surface 22 is a rigid planar surface. In another embodiment, the striking surface 22 is a block, e.g., a steel block, although a metal plate or a golf club head may be equally suitable. In one embodiment, the mass of the block is preferably at least about 50 times greater than the mass of the object 36. In another embodiment, the mass of the block is preferably at least about 100 times greater than the mass of the object 36.

As shown in FIG. 1, the propelling device 34 fires an object 36 at the striking surface 22 such that it passes through the sensing unit 200. Preferably, the object 36 strikes the striking surface 22 (e.g., in a direction relatively normal to the striking surface 22) and then bounces back (e.g., also in a direction relatively normal to the striking surface 22). The sensing unit(s) 200 detects the presence of the object 36, and in cooperation with timers, makes it possible to measure the time required for the object to travel between discrete distances within the space between the propelling device 34 and the striking surface 22. The computing unit 500 computes the COR and contact time of the object 36 using the measurements of time between activation of the sensing unit(s) 200 and discrete distances between sensing unit(s) 200.

The propelling device 34 can be situated in such a way that it fires the object in any direction. Preferably, the striking surface 22 is situated such that the striking surface 22 is perpendicular to the direction in which the propelling device 34 fires the object 36. In a preferred embodiment of the present invention, shown in FIG. 1, the propelling device 34 is situated in such a way that it fires the object 36 in a horizontal direction, i.e., perpendicular to the direction of gravity, denoted as g in FIG. 1, and the striking surface 22 is situated vertically, i.e., perpendicular to the direction in which the propelling device 34 fires the object 36. In another embodiment of the present invention, the propelling device 34 is situated in such a way that it fires the object 36 vertically in the upward direction and the striking surface 22 is situated horizontally, i.e., perpendicular to the direction in which the propelling device 34 fires the object 36.

Figure 2:
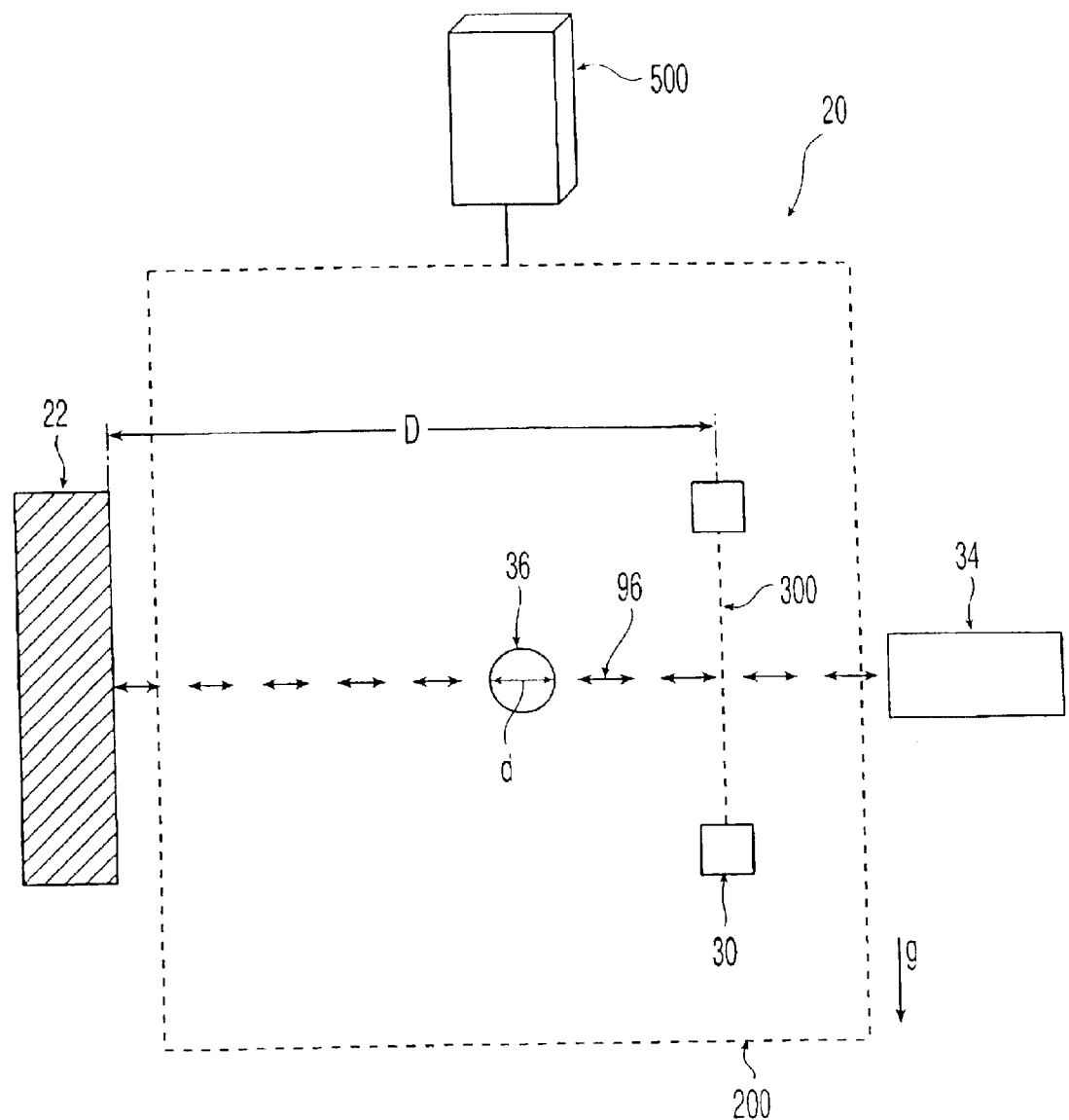
FIG. 2 illustrates one embodiment of the arrangement of the apparatus of FIG. 1 according to the present invention.

FIG. 2 shows another arrangement of the sensing unit 200 within the apparatus 20 shown in FIG. 1. The sensing unit 200 enables a time measurement for an object to travel between discrete points within the space between the propelling device 34 and the striking surface 22. This measurement enables the calculation of the contact time between the object 36 and the striking surface 22. The sensing unit 200 also enables the calculation of the velocity of the object 36 before and after the object 36 contacts the striking surface 22. The calculation of the velocity, in turn, will enable the calculation of the COR of the object, because the COR of the object is the ratio of the outbound or rebound velocity to the inbound or impact velocity as the object strikes the striking surface in the normal direction.

In FIG. 2, the sensing unit 200 includes a sensing device 30, located in the space between the propelling device 34 and the striking surface 22. The sensing device 30 has a sensing field covering a sensing plane 300. The sensing device 30 preferably has an on/off switch such that, when any portion of the object 36 is in the sensing plane 300, the on/off status changes. The timer included in the computing unit 500, in communication with the sensing device 30, starts and stops in accordance with the changes in the on/off status of the sensing device 30. The time duration between the starts and stops is recorded by the central processing unit.

The sensing device 30 may be a sensor with an on/off status that can signal a timer when any portion of an object 36 is in the sensing plane 300, such as a light gate, a ballistics screen, an optical sensor, or the like. In one embodiment, the sensing device 30 is a light gate. In another embodiment, the sensing device 30 is a ballistics screen. In yet another embodiment, the sensing device 30 includes a coherent light source, such as a laser. The laser preferably has a wavelength from about 400 nanometers (nm) and about 800 nm. The laser beam is preferably split into multiple beams to form the sensing plane 300.

In one embodiment, the sensing device 30 includes a plurality of discrete sensors to provide for a widened sensing plane. The plurality of sensors may be arranged in any manner to allow sensing of an object passing through the predetermined plane. In one embodiment, a linear array of individual emitters may be arranged opposite a linear array of individual receivers. In another embodiment, a laser and beam splitter is used to emit light opposite a linear array of individual receivers. The emitters may be arranged across one edge of the predetermined plane of the sensing device and the receivers may be arranged across a directly opposing edge, although the arrangement of the plurality of sensors is not limited merely to these type of conformations. For example, an alternating linear array of individual emitters and receivers can be arranged opposite a similar alternating linear array of individual receivers and emitters. Alternately, either array may include staggering the emitters or receivers or both and/or arranging the emitters or receivers or both in blocks that may alternate, instead of alternating individual emitters and receivers.

Further, according to the invention, the plurality of sensors, or the planar emitters and receivers, may be arranged so that there are an even number of edges from which signals are being emitted and by which signals are being received. In the simplest case, with a planar emitter or a linear array of individual emitters on one edge and a planar receiver or a linear array of individual receivers on a directly opposing edge, the number would be two. In another embodiment, signals can be emitted and received as above, with other signals being emitted and received in the same manner, but oriented orthogonally in the plane to the previous signals. In this embodiment, the signals would criss-cross and the number would be four (i.e., a square or rectangle where each side is capable of emitting or receiving a signal). In another embodiment, three such sets of signals can be emitted and received in the same manner as above, with each signal emitted or received being oriented at 60° to any other emitted or received signal; the number in this case would be six (i.e., a hexagon where each side is capable of emitting or receiving a signal). In yet another embodiment, four sets of signals can be emitted and received in the same manner as above, with each signal emitted or received being oriented at 45° to any other emitted or received signal; the number in this case would be eight (i.e., an octagon where each side is capable of emitting or receiving a signal). Alternately, the plurality of sensors may be arranged so that the individual emitters and receivers are situated opposite each other in any arrangement, so that the shape defined by those emitters and receivers is circular within the predetermined plane of the sensing device.

In FIG. 2, the sensing device 30 is arranged in such a way that the sensing plane 300 is parallel to the striking surface 22. The distance between the sensing plane 300 and the striking surface 22, D, is greater than the dimension of the object 36 (e.g., the diameter of the golf ball), d. After the object 36 is fired from the propelling device 34, it passes through the sensing plane 300. The sensing device 30 transmits a signal to the computing unit 500, causing the timer to start and the central processing unit to record the start time $t_1$, when the foremost point of the object 36 enters the sensing plane 300. The sensing device 30 then sends another signal to the computing unit 500 to register the time $t_2$, when the rearmost point of the object 36 leaves the sensing plane 300. When the object 36 rebounds back from the striking surface 22 and passes through the sensing plane 300, the sensing device 30 transmits another signal to the computing unit 500 to register the time $t_3$, when the foremost point of the object enters the sensing plane 300. The sensing device 30 sends yet another signal to the computing unit 500, registering time $t_4$, when the rearmost point of the object leaves the sensing plane 300.

Based on the assumption that the object 36 travels at a constant speed $v_1$, in a direction normal to the striking surface 22 before striking, and that the sensing plane 300 is parallel to the direction of gravity, the speed $v_1$ can be calculated as the ratio of the dimension of the object 36 to the time duration for the object 36 to go through the sensing plane 300 the first time:

$$v_1 = d/(t_2 - t_1).$$

Similarly, based on the assumption that the object 36 travels at another constant speed $v_2$, in a direction normal to the striking surface 22 after striking it, and that the sensing plane 300 is parallel to the direction of gravity, the speed $v_2$ can be calculated as the ratio of the dimension of the object 36 to the time duration for the object 36 to go through the sensing plane 300 the second time: $v_2 = d/(t_4 - t_3)$.

The Coefficient of the Restitution (COR) can therefore be calculated as $v_2/v_1$, or $(t_2 - t_1)/(t_4 - t_3)$.

Figure 3:
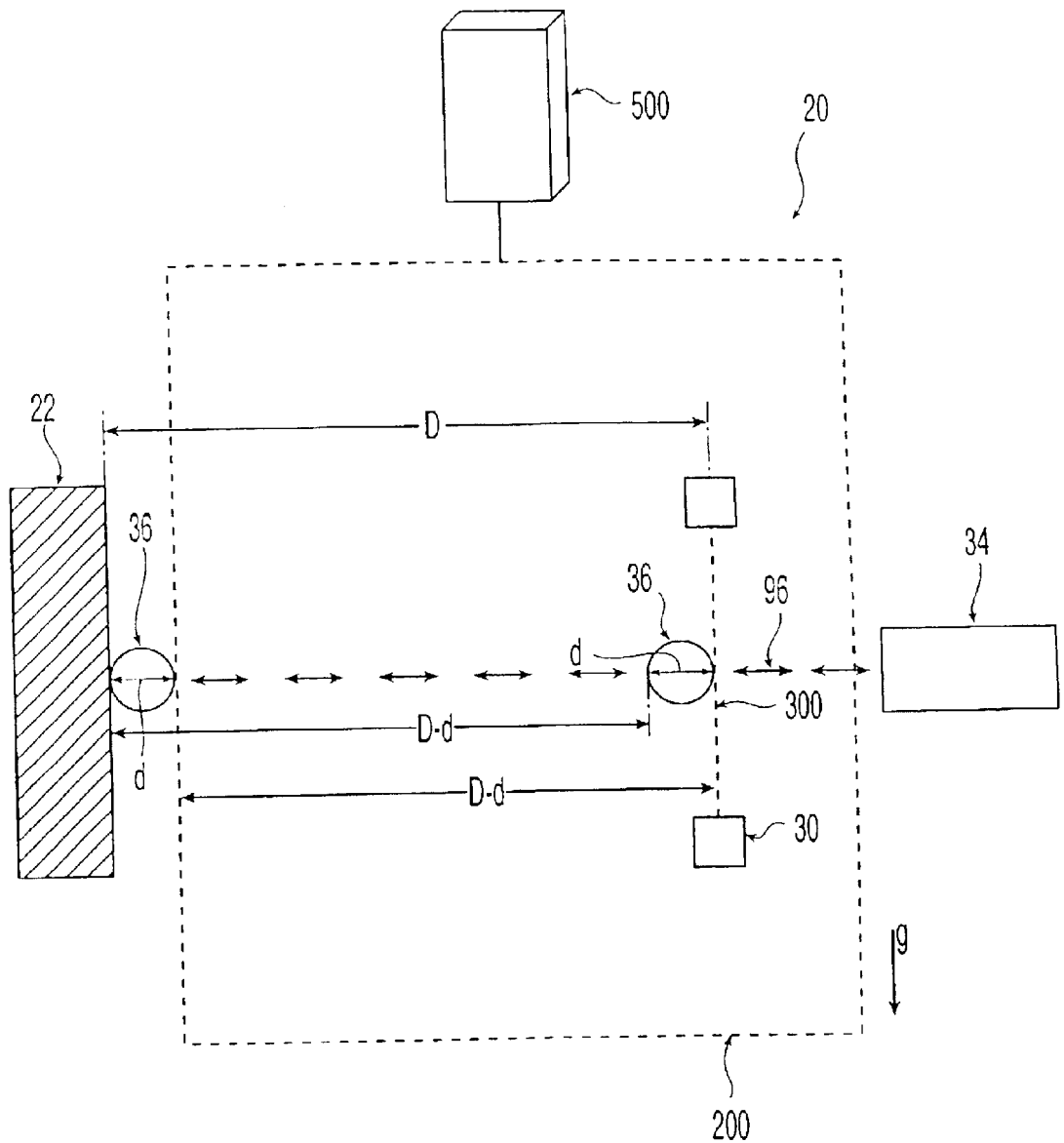
FIG. 3 illustrates an object in motion using the arrangement of the apparatus shown in FIG. 2 according to the present invention.

FIG. 3 illustrates that upon initially leaving the sensing plane 300, the object 36 travels a distance of (D−d) at the speed $v_1$ normal to the striking surface 22 before contact. This takes a time period of $P_1 = (D-d)/v_1$. Likewise, after leaving the striking surface 22, the object 36 travels a distance of (D−d) at the speed $v_2$ normal to the sensing plane 300 before entering the second time. This takes a time period of $P_2 = (D-d)/v_2$.

Because the object 36 stays past the sensing plane 300 (moving toward the striking surface 22) for a total time of $t_3 - t_2$, i.e., after leaving the sensing plane 300 initially and before reentering the sensing plane 300 the second time, the contact time between the object 36 and the striking surface 22, $t_{bc}$, is:

$$t_{bc} = (t_3 - t_2) - P_1 - P_2$$
$$= (t_3 - t_2) - (D-d)/v_2 - (D-d)/v_2$$
$$= (t_3 - t_2) - (D-d)(t_4 - t_3)/d - (D-d)(t_2 - t_1)/d.$$

Figure 4:
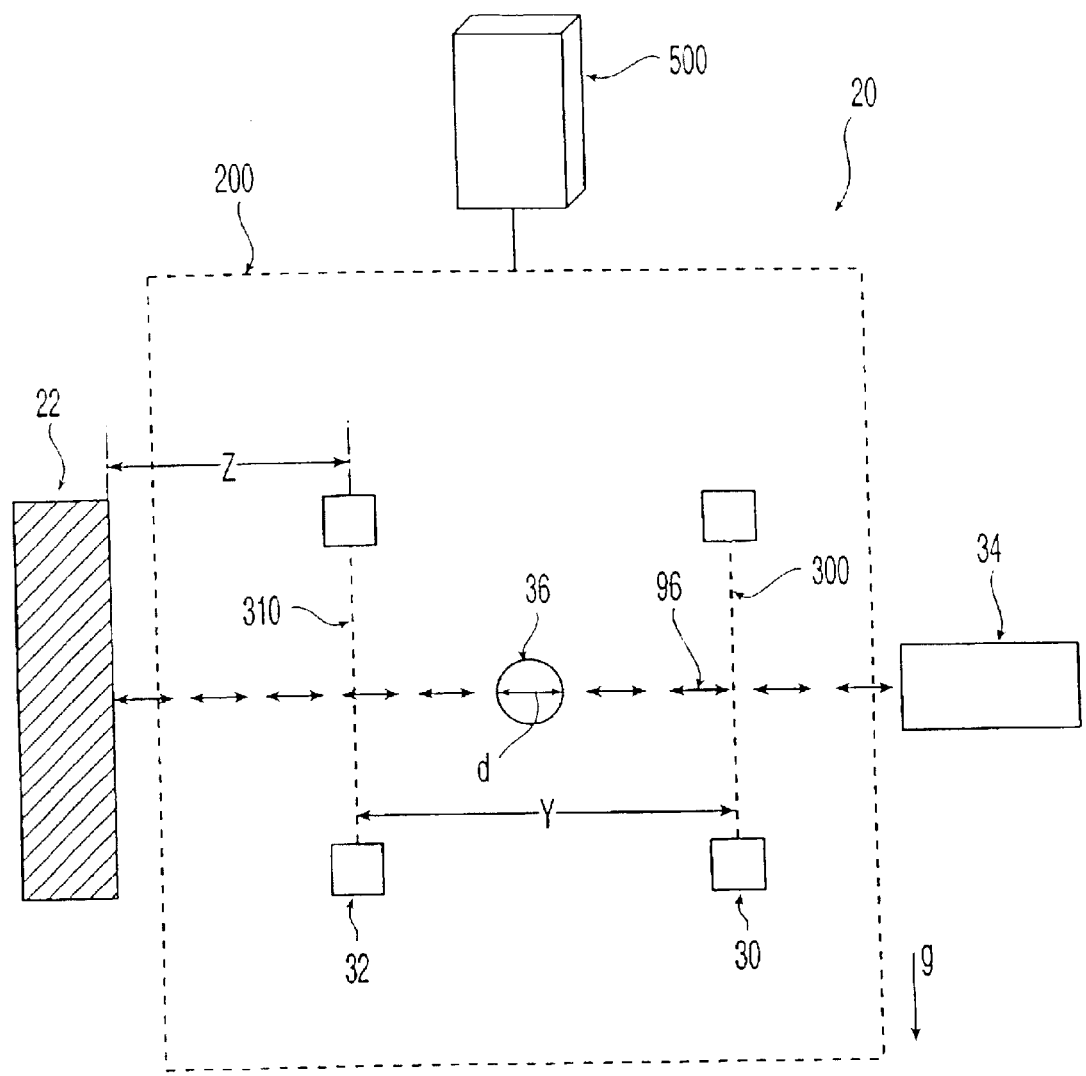
FIG. 4 illustrates one embodiment of the arrangement of the apparatus shown in FIG. 1 using two sensing devices according to the present invention.

FIG. 4 shows another arrangement of the apparatus 20 shown in FIG. 1. In comparison to the embodiment shown in FIGS. 2 and 3, in this embodiment, the sensing unit 200 includes a first sensing device 30 and a second sensing device 32, each having a sensing field covering a first sensing plane 300 and a second sensing plane 310, respectively. The second sensing device 32, located in the space between the first sensing device 300 and the striking surface 22 preferably has an on/off switch such that, when any portion of the object is in the second predetermined plane, the on/off status changes, as discussed with respect to the on/off switch of the sensing device 30 in FIGS. 2 and 3.

The second sensing device 32 may also be a sensor with an on/off status to signal a timer when any portion of an object 36 is in the second sensing plane 310, such as a light gate, a solid ballistics screen, or a fiber optic sensor. In a preferred embodiment, the second sensing device 32 is a light gate. In another preferred embodiment, the second sensing device 32 is a ballistics screen. In yet another preferred embodiment of the present invention, the second sensing device 32 includes a plurality of sensors to provide for a widened second sensing plane 310. In yet another embodiment, the second sensing device 310 includes a coherent light source, such as a laser. The laser preferably has a wavelength from about 400 nanometers (nm) and about 800 nm. The laser beam is preferably split into multiple beams to form the second sensing plane 310.

In FIG. 4, the second sensing device 32 is arranged in such a way that the second sensing plane 310, like the first sensing plane 300, is also parallel to the surface of the striking surface 22. The distance between the second sensing plane 310 and the first sensing plane 300 is Y and the distance between the second sensing plane 310 and the striking surface 22 is Z. Similar to FIGS. 2 and 3, Z is greater than d, the dimension of the object.

After the object 36 is fired from the propelling device 34, it passes through the first sensing plane 300 and then the second sensing plane 310. The first sensing device 30 sends a signal to the computing unit 500, causing the timer in the computing unit to start and the central processing unit to record the time $t_1$, when the foremost point of the object 36 enters the first sensing plane 300. The second sensing device 32 also sends a signal to the computing unit 500, causing the timer in the computing unit to start at time $t_2$ and the central processing unit to record the time $t_2$, when the foremost point of the object 36 enters the second sensing plane 310. When the object 36 rebounds back from the striking surface 22 and passes through the second sensing plane 310 and then the first sensing plane 300, the second sensing device sends another signal to the computing unit 500 to register the time $t_3$, when the foremost point of the object 36 enters the second sensing plane 310 the second time. The first sensing device 30 also sends a signal to the computing unit 500 to register the time $t_4$, when the foremost point of the object 36 enters the first sensing plane 300 the second time.

Based on the assumption that the object 36 travels at a constant speed $v_1$, in a direction normal to the striking surface 22 before contact, and that the sensing planes 300, 310 are parallel to the direction of gravity, the speed $v_1$ can be calculated as the ratio of the predetermined distance Y between the first sensing plane 300 and the second sensing plane 310 to the time duration for the object 36 to travel between the sensing planes:

$$v_1 = Y/(t_2 - t_1).$$

Similarly, based on the assumption that the object 36 travels at another constant speed $v_2$, in a direction normal to the striking surface after contact, and that the sensing planes 300, 310 are parallel to the direction of gravity, the speed $v_2$ can be calculated as the ratio of the predetermined distance Y between the first and the second sensing planes 310 to the time duration for the object 36 to travel between the sensing planes:

$$v_2 = Y/(t_4 - t_3).$$

The Coefficient of the Restitution (COR) can therefore be calculated as $v_2/v_1$, or $(t_2 - t_1)/(t_4 - t_3)$.

Similar to the situation shown in FIG. 3, after entering the second sensing plane 310 the first time, the object 36 travels a distance of Z at the speed $v_1$, in a direction normal to the striking surface 22 before contact. This time period is $P_1 = Z/v_1$. Likewise, after leaving the striking surface 22, the object 36 travels a distance of (Z−d) at the speed $v_2$, normal to the second sensing plane 310, before entering it the second time. This time period is $P_2 = (Z-d)/v_2$.

Because the object 36 stays past (toward the striking surface with respect to) the second sensing plane 310 for a total time of $t_3 - t_2$, i.e., after leaving the second sensing plane 310 the first time and before entering the second sensing plane 310 the second time, the contact time between the object 36 and the striking surface 22, $t_{bc}$, is:

$$t_{bc} = (t_3 - t_2) - P_1 - P_2$$
$$= (t_3 - t_2) - (Z-d)/v_2 - (Z-d)/v_1$$
$$= (t_3 - t_2) - (Z-d)(t_4 - t_3)/Y - Z(t_2 - t_1)/Y.$$

Although FIG. 4 is a more complex arrangement and requires two sensing devices, instead of only one sensing device as shown in FIGS. 2 and 3, this arrangement has a distance Y between the two sensing planes, which is significantly larger than that dimension d of the object 36. This difference in dimensions provides enhanced accuracy for the velocity measurement of the object 36. In one embodiment, the distance Y is about 12 inches or greater. In another embodiment, the predetermined distance Y is about 4 feet or greater.

Figure 5:
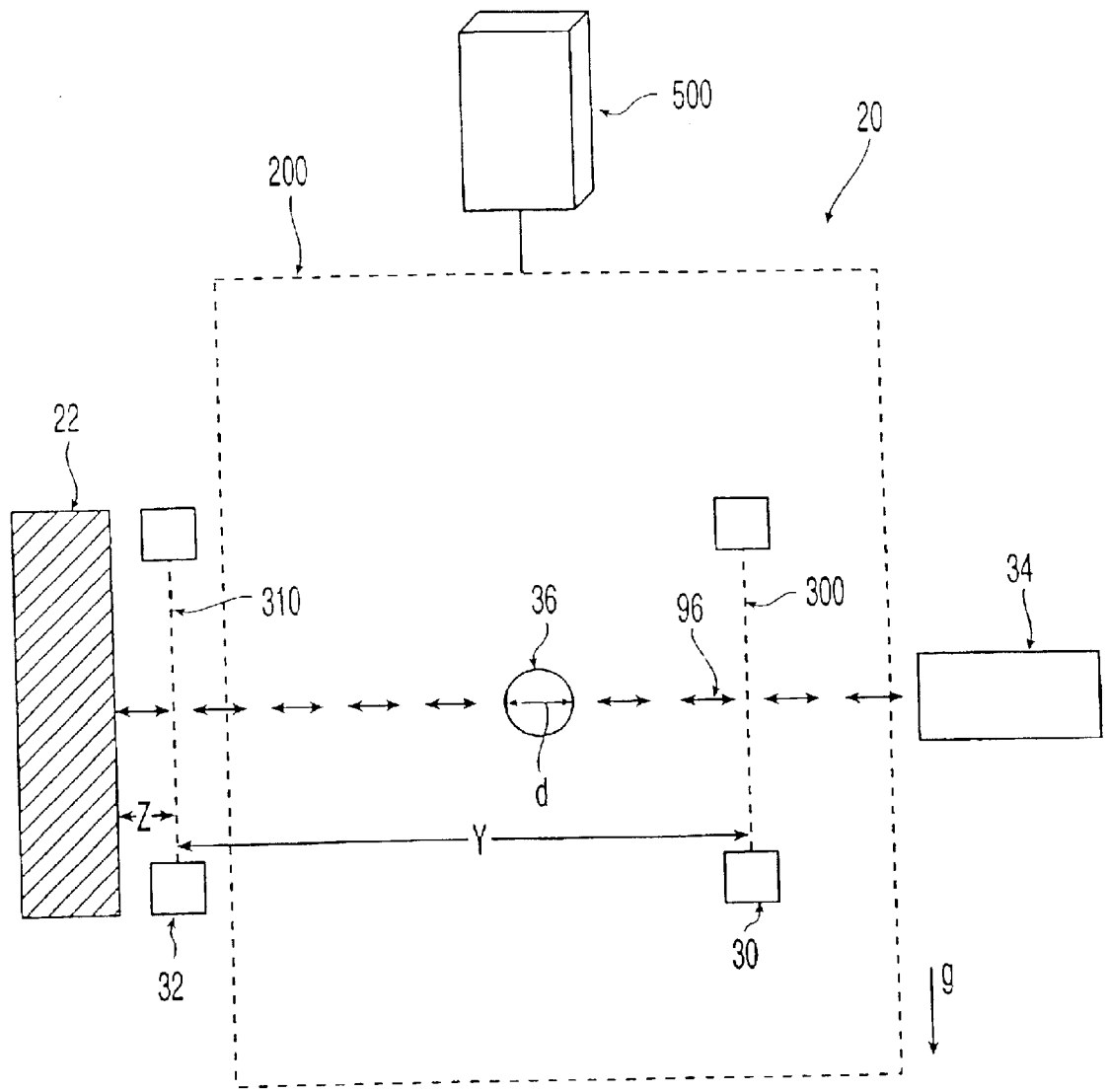
FIG. 5 illustrates another embodiment of the arrangement of the apparatus shown in FIG. 1 using two sensing devices according to the present invention.

FIG. 5 shows another arrangement of the apparatus 20 using two sensing devices. In this arrangement, the second sensing device 32 is located much closer to the striking surface 22 than as illustrated in FIG. 4. Consequently, the distance between the second sensing plane 310 and the striking surface, Z, is less than the dimension, d, of the object 36. In this embodiment, the first and second sensing devices 30, 32 send signals to the computing unit 500 in the same way prior to the object contacting the striking surface 22, i.e., after the object 36 is fired from the propelling device 34, it passes through the first sensing plane 300 and then the second sensing plane 310. The first sensing device 30 sends a signal to the computing unit 500 to register the time $t_1$, when the foremost point of the object enters the first sensing plane 300. The second sensing device 32 also sends a signal to the computing unit 500 to register the time $t_2$, when the foremost point of the object 36 enters the second sensing plane 310.

However, the first and second sensing devices 30, 32 send signals to the computing unit 500 in a different way after the object contacts the striking surface 22. Because the distance between the second sensing plane 310 and the striking surface 22, Z, is less than d, the dimension of the object, the object can not leave the second sensing plane 310 before contacting the striking surface 22. The object is also not able to enter the second sensing plane 310 a second time after contacting the striking surface 22. Instead, the object remains in the second sensing plane 310 when in contact with the striking surface 22. Thus, when the object 36 rebounds back from the striking surface 22, the second sensing device 32 sends a signal to the computing unit 500 to register the time $t_3$, when the rearmost point of the object 36 leaves the second sensing plane 310, instead of when the foremost point of the object enters the second sensing plane 310 the second time. The first sensing device 30, like before, sends a signal to the computing unit 500 to register the time $t_4$, when the foremost point of the object enters the first sensing plane 300 the second time.

Based on the assumption that the object travels at a constant speed $v_1$, in a direction normal to the striking surface before contact, and that the sensing planes 300, 310 are parallel to the direction of gravity, the speed $v_1$ can be calculated as the ratio of the distance Y between the sensing planes 300, 310 to the time duration for the object to travel between the first and second sensing planes 300, 310 the first time:

$$v_1 = Y/(t_2 - t_1).$$

Similarly, based on the assumption that the object travels at another constant speed $v_2$, in a direction normal to the striking surface after contact, and that the sensing planes 300, 310 are parallel to the direction of gravity, the speed $v_2$ can be calculated as the ratio of the distance Y between the first and the second predetermined planes minus the object diameter d to the time duration for the object to travel between the sensing planes 300, 310 the second time:

$$v_2 = (Y-d)/(t_4 - t_3).$$

The Coefficient of the Restitution (COR) can therefore be calculated as $v_2/v_1$, or $(Y-d)(t_2-t_1)/[Y(t_4-t_3)]$.

After entering the second sensing plane 310, the object 36 travels a distance of D at the speed $v_1$ normal to the striking surface 22 before contact. This requires a time period of $P_1 = D/v_1$. Likewise, after leaving the striking surface, the object travels a distance of D at the speed $v_2$ normal to the second sensing plane 310 before leaving the second sensing plane 310. This requires a time period of $P_2 = D/v_2$.

Because the object 36 stays within the second sensing plane 310 for a total time of $t_3 - t_2$ after entering and before leaving the second sensing plane 310, the contact time the object 36 makes with the striking surface 22, $t_{bc}$, is:

$$\begin{aligned} t_{bc} &= (t_3 - t_2) - P_1 - P_2 \\ &= (t_3 - t_2) - Z/v_2 - Z/v_1 \\ &= (t_3 - t_2) - Z(t_4 - t_3)/(Y-d) - Z(t_2 - t_1)/Y. \end{aligned}$$

As discussed with respect to the embodiment shown in FIG. 4, although FIG. 5 shows a more complex dual sensing device arrangement, the distance Y between the two sensing planes 300, 310, which is significantly larger than the dimension of the object d, provides a more accurate measurement of the velocity of the object 36 and contact time with the striking surface 22.

In order for this embodiment to provide accurate measurements, the distance Z between the second sensing plane 310 and the striking surface 22 must be small. In a preferred embodiment of the present invention, the distance Z is about 1 inch or less. In another preferred embodiment of the present invention, the distance Z is about 0.25 inches or less. In yet another preferred embodiment of the present invention, the distance Z is about 0.13 inches or less.

Figure 6:
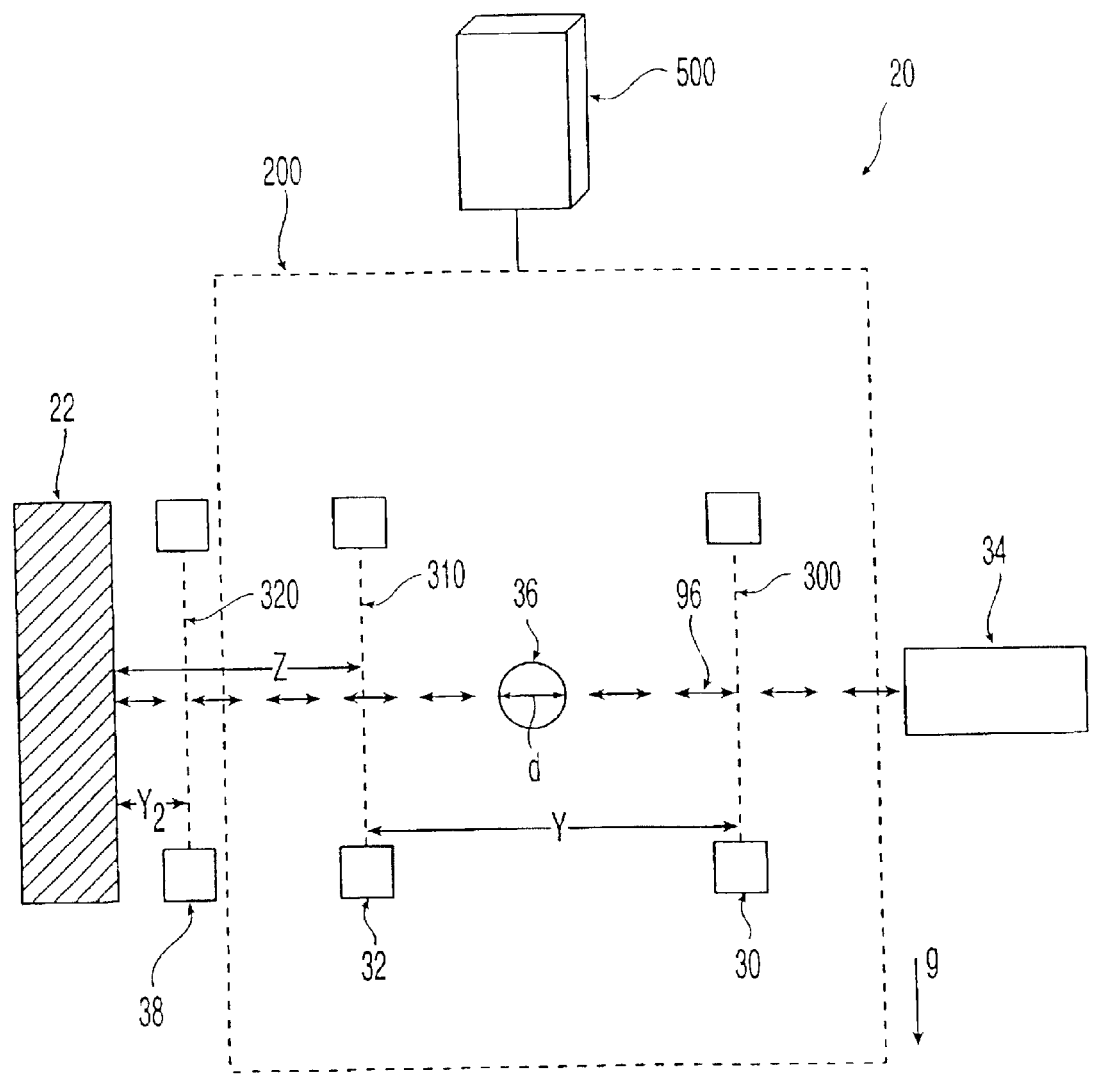
FIG. 6 illustrates another embodiment of the arrangement of the apparatus shown in FIG. 1 using three sensing devices according to the present invention.

FIG. 6 shows another arrangement of apparatus 20 of the present invention. In this embodiment, the sensing unit further includes a third sensing device 38, in addition to the first sensing device 30 and second sensing device 32 of FIGS. 4 and 5. The third sensing device 38 is located near the striking surface 22. It has a sensing area covering an third sensing plane 320 that is parallel to the striking surface 22. The third sensing device 38 is designed specifically for the purpose of enabling the registration of the time duration during which any part of the object 36 is in the third sensing plane 320. According to this embodiment, after the object 36 is fired from the propelling device 34, the first and second sensing devices 30, 32 signal the computing unit 500 to register the time duration $t_1$ between the time when the foremost point of the object 36 enters the first sensing plane 300 and the time when the foremost point of the object 36 enters the second sensing plane 310. The computing unit 500 also registers the time duration $T_b$ during which the object 36 stays in the third sensing plane 320. When the object 36 rebounds back from the striking surface 22, the sensing devices signal the computing unit 500 to register the time duration $t_2$ between the time when the foremost point of the object 36 enters the second sensing plane 310 the second time and the time when the foremost point of the object enters the first sensing plane 300 the second time.

Based on the assumption that the object 36 travels at a constant speed $v_1$, in a direction normal to the striking surface 22 before contact, and that the sensing planes are parallel to the direction of gravity, the speed $v_1$ can be calculated as the ratio of the predetermined distance Y between the first and the second sensing planes 300, 310 to the time duration for the object to travel between the two sensing planes the first time:

$$v_1 = Y/t_1.$$

Similarly, based on the assumption that the object travels at another constant speed $v_2$, in a direction normal to the striking surface 22 after contact, the speed $v_2$ can be calculated as the ratio of the predetermined distance Y between the first and the second sensing planes 300, 310 to the time duration for the object to travel between the two sensing planes the second time:

$$v_2 = Y/t_2.$$

The Coefficient of the Restitution (COR) can therefore be calculated as $v_2/v_1$, or $t_1/t_2$, and the contact time between the object 36 and the striking surface 22, $t_{bc}$, can be considered equivalent to the time duration $T_b$ during which the object 36 stays in the second sensing plane 310 minus the inbound and outbound flight time to transit the distance $Y_2$. Thus, $t_{bc} = T_b - Y_2/v_1 - Y_2/v_2$.

In order for this embodiment to provide accurate measurements, the distance $Y_2$ between the third sensing plane 320 and the striking surface 22 must be small. In a preferred embodiment of the present invention, the distance $Y_2$ is about 1 inch or less. In another preferred embodiment of the present invention, the distance $Y_2$ is about 0.25 inches or less. In yet another preferred embodiment of the present invention, the distance $Y_2$ is about 0.13 inches or less.

The striking surface 22 in this embodiment is preferably a rigid block or metal plate. The apparatus 20 is preferably set up to operate in a horizontal position with the sensing planes 300, 310, 320 parallel to the direction of gravity.

In one embodiment, the third sensing device 38 is a fiber optic sensor including a planar optical emitter and a planar optical receiver adjacent to the striking surface 22. The use of fiber optic sensors is advantageous because: (1) balls and cores are usable without modification of the apparatus; (2) fiber optic components and associated electronic signal processing hardware may be designed to operate at switching frequencies of 500 kHz which resolves contact time to an accuracy of 2 microseconds; and (3) the use of fiber optics significantly reduces problems associated with radio frequency induced electronic noise.

Contact time may also be measured by placing conductive foil on the object 36 and by placing a lattice of conductors on the striking surface 22. When the object 36 is in contact with the striking surface 22, the resistance of the lattice can vary measurably. Contact duration is generally linked to the duration of the resistance change. This technique is effective but can have deficiencies in comparison to the optical technique. The deficiencies can include: 1) alteration of the balls or cores to have conductive surfaces; 2) the conductive lattice sustaining damage after repeated impact; and 3) the electronic circuits required to measure resistance variations are prone to radio frequency noise and do not operate at as high a frequency as the optical technique disclosed above.

Figure 7:
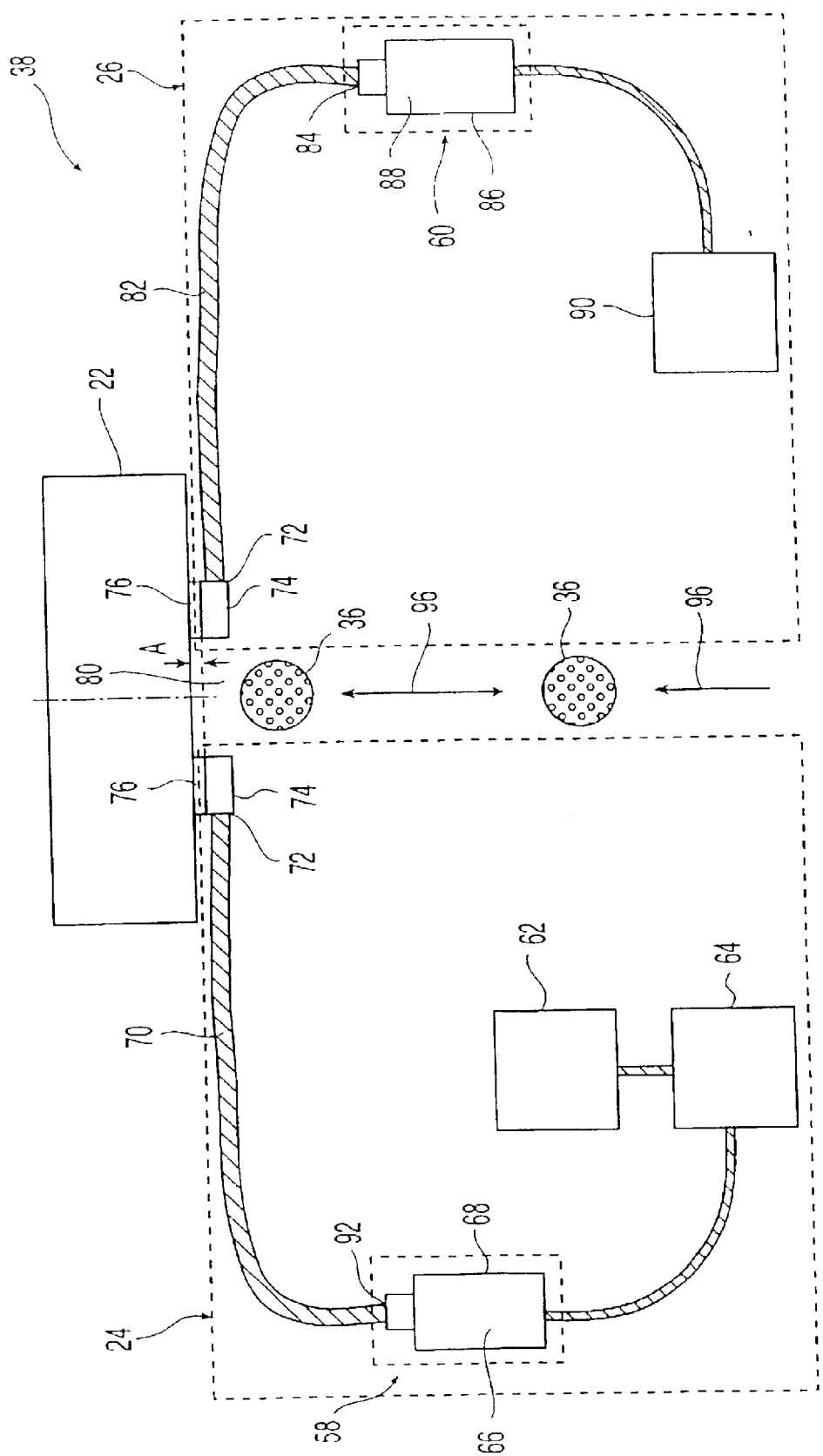
FIG. 7 is a schematic of the third optical sensor in accordance with a preferred embodiment of FIG. 6 according to the present invention.

FIG. 7 shows a preferred third sensing device 38 in detail. The third sensing device 38 includes a light or other energy source 58 and receiver 60. The planar emitter 24, or other energy transmitter, preferably includes a number of components. A power supply 62, e.g., such as a regulated 12 volt 0.5 amp DC power supply, is connected to an adjustable monolithic regulator 64. This adjustable voltage is applied to an energy emitter 66, such as a lamp, e.g., a #349 miniature incandescent lamp, that is preferably within an enclosed housing 68. The housing 68 should generally accept a standard fiber optic assembly 70, e.g., such as one that has a thin, flat dispersion at the opposed end 72. The opposed end may be held in position, e.g., by a Ultra High Molecular Weight polyethylene panel (UHMW panel) 74, held and constrained in position by flat ceramic magnets 76. Typically, the panel 74 is slightly removed from the striking surface 22 by a short distance A, which is preferably about 0.25 inches or less, and is cut away to form an opening 80 in the center such that a golf ball may pass through and strike the rigid block 78. A fiber assembly 70 is placed at this opening 80 and opposes a second fiber assembly 82 directly across the opening 80, which forms part of the optical planar receiver 26. At the opposite end 84, 92 of each fiber assembly 82, 70 is an identical fiber assembly contained within an enclosed housing 68, 86 is an optic receiver 66, 88.

In a preferred embodiment, each optic receiver 66, 88 is an inverting fiber optic receiver, e.g., such as Honeywell Model HFD-3031. Each inverting fiber optic receiver is electrically connected to the input of a counter/timer computer interface card 64, 90. The counter/timer computer interface card 64, 90 preferably has an operating frequency of about 500 kHz or greater, more preferably about 1 MHz or greater. The operating frequency should be advantageously selected to provide as much accuracy and resolution as possible for contact time and COR measurements.

Figure 8:
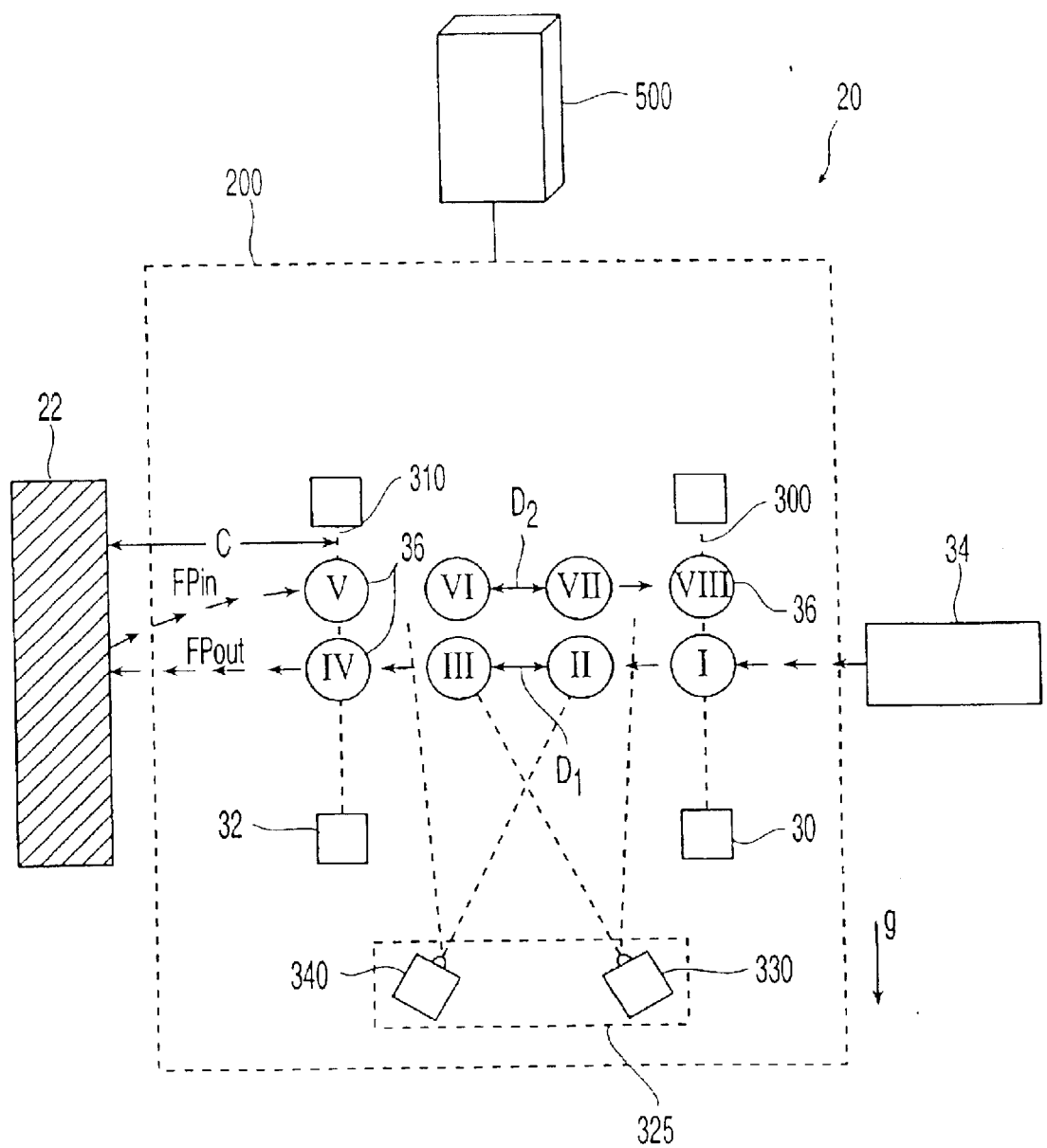
FIG. 8 illustrates another embodiment of the arrangement of the apparatus shown in FIG. 1, using optical cameras according to the present invention.

Another embodiment of the present invention is shown in FIG. 8, similar to the arrangement shown in FIG. 4 using two sensing devices in combination with one or more optical cameras. In this embodiment, the sensing unit 200 includes a first sensing device 30 and a second sensing device 32, each having a sensing field covering a first sensing plane 300 and a second sensing plane 310, respectively, that are parallel to the surface of the striking surface 22. A camera system 325 includes at least one camera and lighting unit. At least two optical cameras are preferred to triangulate the space with triggers and timers. FIG. 8 illustrates this embodiment in which the camera system 325 includes a first camera 330 and a second camera 340, positioned in between the sensing planes 300, 310.

The sensing devices 30, 32 may also be sensors with an on/off status to simultaneously signal at least one timer in the computing unit 500 and the camera system 325 when any portion of an object 36 passes through the first or second sensing planes 300, 310. For example, the sensing devices 30, 32 may be coherent light sources, such as lasers. The sensing devices 30, 32 may communicate via an asynchronous protocol through the computing device 500 to the camera system 325 and timers to control activation.

The camera system 325 preferably includes a lighting system, such as a dual strobe lighting unit, and a filtering system, for each camera used. The cameras 330, 340 used in this embodiment are preferably electro-optical cameras with light-receiving apertures, shutters, and light sensitive silicon panels as discussed in U.S. Pat. No. 5,575,719, which is incorporated in its entirety by reference herein. Multishutter cameras may also be used as disclosed in co-pending application Ser. No. 09/379,592, the contents of which are incorporated in its entirety by reference herein. Suitable commercially available cameras include, but are not limited to, ELECTRIM EDC-1000U Computer Cameras (EDC Cameras) from Electrim Corporation in Princeton, N.J. Charge coupled device or CCD cameras are preferred, but TV-type video cameras are also useful.

In one embodiment, the camera is a CCD camera with about 90,000 pixels or greater. In a preferred embodiment, the camera has about 300,000 pixels or greater, and, more preferably, the camera has about 1,000,000 pixels.

FIG. 8 illustrates an object 36 in various positions I-IV after firing from the propelling device 34 on the outbound trip to the striking surface 22, and on the return (inbound) flight, V-VIII, after contacting the striking surface 22. After the object 36 is fired from the propelling device 34, it passes through the first sensing plane 300. When the foremost point of the object 36 enters the first sensing plane 300 (Position I), the first sensing device 30 sends a signal to the computing unit 500 to activate the camera system 325. Once activated, the cameras 330, 340 each acquire a first image, e.g., Position II. After a known time interval ($t_c$), the cameras 330, 340 each acquire a second image, e.g., Position III.

The object 36 then moves through the second sensing plane 310 (Position IV) and the computing unit 500 receives a signal from the sensing device 32 to store a time $t_2$. The object 36 then continues along the flight path ($FP_{out}$), impacts the striking surface 22, and rebounds, following the inbound flight path ($FP_{in}$). As the object 36 moves into Position V, the sensing device 32 again activates the cameras 340, 330 and sends a signal to the computing unit to record a time $t_3$. The cameras 340, 330 each acquire a pair of images, e.g., Positions VI and VII.

The first and second images acquired by each camera make it possible to triangulate the spacial coordinates of the object 36 at each image capture, which allows for the determination of the distance between the object 36 at Positions II and III, and Positions VI and VII, to be determined. In another embodiment, however, a dual camera system is used, but each camera has a single flash. In yet another embodiment, a single camera is used. Because a dual camera system is used, the.

Based on the assumption that the object 36 travels at a constant speed $v_1$, in a direction normal to the striking surface 22 before contact, and that the sensing planes 300, 310 are parallel to the direction of gravity, the speed $v_1$ can be calculated as the ratio of the distance $D_1$ between the first and second image and the time between each image capture $t_c$:

$$v_1 = D_1/t_c.$$

Similarly, based on the assumption that the object 36 travels at another constant speed $v_2$ on the inbound flight path ($FP_{in}$) after contact, in a direction normal to the striking surface, and that the sensing planes 300, 310 are perpendicular to the direction of gravity, the velocity $v_2$ can be calculated as the ratio of the distance $D_2$ between the first and second images and the time between each image capture $t_c$:

$$v_2 = D_2/t_c.$$

The Coefficient of the Restitution (COR) can therefore be calculated as $v_2/v_1$, or $D_2/D_1$.

Similar to the situation shown in FIG. 4, after passing through the sensing unit 32 (Position IV), wherein time $t_2$ is logged, the object travels a distance of C at the speed $v_1$, in a direction normal to the striking surface 22 before contact. This time period is $P_1 = C/v_1$. Likewise, after leaving the striking surface 22, the object 36 travels a distance of C at the speed $v_2$, in a direction normal to the second sensing plane 310, before passing back through the sensing unit 32 at time $t_3$ (Position V). This time period is $P_2 = C/v_2$.

Because the object 36 stays past (toward the striking surface with respect to) the sensing unit 32 for a total time of $t_3 - t_2$, the contact time between the object 36 and the striking surface 22, $t_{bc}$, is:

$$\begin{aligned} t_{bc} &= (t_3 - t_2) - P_1 - P_2 \\ &= (t_3 - t_2) - C/v_1 - C/v_2 \\ &= (t_3 - t_2) - C(t_c)/D_1 - C(t_c)/D_2. \end{aligned}$$

Any number of ways can be used to calibrate the apparatus 20. For example, when calibrating the system using sensing devices, but no optical cameras, an object 36 may be attached to a measurement device, e.g., such as a dial indicator (not shown). The object is 30 introduced into the path 96 of the normal flight of the object 36 toward the striking surface 22, as shown in FIG. 7. When sufficient light is obstructed, the optic receiver will indicate a HIGH reading. The distance between the striking surface 22 and the position of the object 36 when the receiver indicates a HIGH signal is measured. In the embodiment shown in FIG. 6, this distance is $Y_2$ and is required in the computation of the contact time. The time it takes for the object 36 to contact the striking surface 22 and rebound through the distance $Y_2$ can be subtracted from the duration of time that the HIGH signal is maintained to correct the contact time measurement.

EXAMPLES

These and other aspects of the present invention may be more fully understood by reference to the following tests. While these tests are meant to be illustrative of the apparatus made according to the present invention, the present invention is not meant to be limited by the following tests.

Testing was performed on various balls using the apparatus of the present invention. As is shown in Table 1 below, the HP Eclipse™, a double core ball, and the DT™ two-piece, a two-piece ball, have similar compressions when measured on an Atti compression machine, yet their contact times or impact stiffness measured at a velocity of about 250 ft/s are significantly different. The HP Eclipse™ has a much longer contact time or lower impact stiffness, and a softer feel.

TABLE 1

| Ball | Atti Compression | Velocity | COR | Contact Time |
|---|---|---|---|---|
| DT 2-Piece ™ | 92.7 | 254.43 | 0.817 | 422.9 |
| HP Eclipse ™ | 92.2 | 250.67 | 0.793 | 451.4 |

Thus, contact time is a better measure of ball stiffness than static compression testing.

While it is apparent that the illustrative embodiments of the invention herein disclosed fulfills the objectives stated above, it will be appreciated that numerous modifications and other embodiments may be devised by those skilled in the art. For example, another device could be used for shooting the object out toward the massive block, the device may be oriented at any angle with respect to gravity, or other calculations based on simple trigonometric functions may be employed along with the recorded measurements to account for the effect of the gravitational force on the calculation of the COR. In addition, it will be appreciated that numerous combinations of described and inferred embodiments may be devised by those skilled in the art. For example, the automatic testing apparatus may be combined with the method for measuring contact time. In other embodiments, the automatic testing devices may be combined with the method for calculating COR that is described with reference to FIGS. 1–8. Therefore, it will be understood that the appended claims are intended to cover all such modifications and embodiments which come within the spirit and scope of the present invention.

Although the present invention has been described with reference to particular embodiments, it will be understood to those skilled in the art that the invention is capable of a variety of alternative embodiments within the spirit of the appended claims.

What is claimed is:

1. An apparatus for measuring the physical properties of a golf ball, the apparatus comprising:
    a striking surface;
    a propelling device facing the striking surface that fires the golf ball toward the striking surface, wherein said propelling device comprises an interchangeable barrel system;
    a sensing unit located between the striking surface and the propelling device, wherein the sensing unit has a measuring field covering a space between the propelling device and the striking surface, and wherein the sensing unit is capable of measuring the time it takes for the golf ball to travel a distance in the measuring field of the sensing unit; and
    a computing unit that calculates the Coefficient of Restitution of the golf ball, wherein the computing unit is in communication with the sensing unit.

2. The apparatus according to claim 1, wherein said interchangeable barrel system comprises an inner barrel and an outer barrel, wherein said inner barrel is interchangeable.

3. The apparatus according to claim 2, wherein said inner barrel has a sliding connection with said outer barrel.

4. The apparatus according to claim 2, wherein said outer barrel has an opening for loading balls into said barrel system.

5. The apparatus according to claim 2, wherein said barrel system is positioned at a predetermined angle relative to a horizontal plane.

6. The apparatus according to claim 5, wherein said predetermined angle is between about 0.01 and about 3.0 degrees.

7. The apparatus according to claim 1, wherein said striking surface and said propelling device are positioned at an angle that is not orthogonal.

8. The apparatus according to claim 7, wherein said angle is between about 90 and about 95 degrees.

9. The apparatus according to claim 1, wherein said sensing unit comprises at least two sensors.

10. The apparatus according to claim 9, wherein one of said sensors is positioned substantially close to said striking surface to calculate impact duration between said golf ball and said striking surface.

11. The apparatus according to claim 2, wherein said barrel system comprises a fast acting valve that closes substantially as soon as said object leaves said barrel system.

12. The apparatus according to claim 2, wherein said inner barrel comprises a leading edge having a predetermined angle.

13. The apparatus according to claim 12, wherein said outer barrel comprises a tubular backstop attached to said outer barrel.

14. The apparatus according to claim 13, wherein said ball is positioned based on said leading edge and said tubular backstop.

15. The apparatus according to claim 12, wherein said angle is between about 30 and about 50 degrees.

16. The apparatus according to claim 1, further comprising a pneumatically controlled return system.

17. The apparatus according to claim 16, wherein said return system comprises a valve that directs said balls.

18. The apparatus according to claim 16, wherein said return system uses gravity to collect said balls.

19. The apparatus according to claim 2, wherein the diameter of said inner barrel is between about 0.038 and 0.042 inches greater than the diameter of said ball.

20. The apparatus according to claim 2, wherein the diameter of said outer barrel is between about 0.030 and 0.050 inches greater than the diameter of said inner barrel.

21. The apparatus according to claim 1, wherein said computing unit automatically captures data, calculates Coefficient of Restitution, and counts the number of tests.

22. A method of measuring Coefficient of Restitution of a plurality of golf balls comprising the steps of:
   providing a propelling device, a striking surface, and a sensing unit located between the striking surface and the propelling device;
   automatically firing the plurality of golf balls towards the striking surface with the propelling device;
   measuring a first velocity of the golf balls before it contacts the striking surface;
   measuring a second velocity of the golf balls after it rebounds from the striking surface; and
   calculating the Coefficient of Restitution.

23. The method according to claim 22, further comprising:
   collecting said golf balls after it rebounds from the striking surface;
   re-firing the golf balls towards the striking surface with the propelling device;
   measuring a first velocity of the golf balls before it contacts the striking surface;
   measuring a second velocity of the golf balls after it rebounds from the striking surface; and
   calculating the Coefficient of Restitution.

24. The method according to claim 23, wherein said collecting comprises one of:
   directing said golf balls to said propelling device; and
   directing said golf balls to a collection device.

25. The method according to claim 23, wherein each of said plurality of golf balls are fired individually.

26. The method according to claim 22, further comprising measuring the contact time of said plurality of golf balls.

* * * * *